(12) United States Patent
Alheidt et al.

(10) Patent No.: US 10,898,344 B2
(45) Date of Patent: *Jan. 26, 2021

(54) EXPANDABLE IMPLANT

(71) Applicant: Stryker European Operations Holdings LLC, Kalamazoo, MI (US)

(72) Inventors: Thomas A. Alheidt, Sussex, NJ (US); Bryan D. Milz, Florida, NY (US); Dan Boljonis, Middletown, NJ (US); Julien Doreau, Illats (FR); Christine Herrmann, Fair Lawn, NJ (US)

(73) Assignee: Stryker European Operations Holdings LLC, Wilmington, DE (US)

( * ) Notice: Subject to any disclaimer, the term of this patent is extended or adjusted under 35 U.S.C. 154(b) by 256 days.

This patent is subject to a terminal disclaimer.

(21) Appl. No.: 15/959,716

(22) Filed: Apr. 23, 2018

(65) Prior Publication Data
US 2018/0303625 A1 Oct. 25, 2018

Related U.S. Application Data

(63) Continuation of application No. 15/091,058, filed on Apr. 5, 2016, now Pat. No. 9,962,270, which is a
(Continued)

(51) Int. Cl.
*A61F 2/44* (2006.01)
*A61F 2/46* (2006.01)
*A61F 2/30* (2006.01)

(52) U.S. Cl.
CPC .............. *A61F 2/447* (2013.01); *A61F 2/442* (2013.01); *A61F 2/4611* (2013.01);
(Continued)

(58) Field of Classification Search
CPC .. A61F 2/44; A61F 2/442; A61F 2/447; A61F 2/46
See application file for complete search history.

(56) References Cited

U.S. PATENT DOCUMENTS 2,799,196 A  7/1957  Alvarez
3,426,364 A  2/1969  Lumb
(Continued)

FOREIGN PATENT DOCUMENTS

CA  1333209 C  11/1994
DE  3729600 A1  3/1989
(Continued)

OTHER PUBLICATIONS

International Search Report and Written Opinion for Application No. PCT/US2012/051083 dated Dec. 20, 2012.
(Continued)

*Primary Examiner* — Christopher J Beccia
(74) *Attorney, Agent, or Firm* — Lerner, David, Littenberg, Krumholz & Mentlik, LLP

(57) ABSTRACT

An expandable implant is disclosed in which the implant includes top and bottom plates having angled inner surfaces that interact with expansion members. The expansion members may be situated on an actuator, and may include at least one vertical projection. In some instances, rotation of the actuator in opposing directions about a longitudinal axis may cause the expansion members to move toward or away from one another, thereby resulting in separation of the top and bottom plates. During such expansion of the implant, the at least one vertical projection of the expansion members may be guided at least partially within a recess formed in the first or second plate. Pins may also be included with the expansion members that ride along respective slots in the plates during expansion. An insertion instrument for implanting the aforementioned implant, and methods of using the same, are also disclosed.

20 Claims, 15 Drawing Sheets

Related U.S. Application Data continuation of application No. 13/587,205, filed on Aug. 16, 2012, now Pat. No. 9,320,610.

(60) Provisional application No. 61/523,981, filed on Aug. 16, 2011.

(52) U.S. Cl.
CPC ....... *A61F 2/4603* (2013.01); *A61F 2002/304* (2013.01); *A61F 2002/3039* (2013.01); *A61F 2002/3055* (2013.01); *A61F 2002/30281* (2013.01); *A61F 2002/30397* (2013.01); *A61F 2002/30405* (2013.01); *A61F 2002/30433* (2013.01); *A61F 2002/30507* (2013.01); *A61F 2002/30523* (2013.01); *A61F 2002/30556* (2013.01); *A61F 2002/30579* (2013.01); *A61F 2002/30594* (2013.01); *A61F 2002/30601* (2013.01); *A61F 2002/30607* (2013.01); *A61F 2002/30622* (2013.01); *A61F 2002/30777* (2013.01); *A61F 2002/30785* (2013.01); *A61F 2002/30827* (2013.01); *A61F 2002/30843* (2013.01); *A61F 2002/30878* (2013.01); *A61F 2002/30892* (2013.01); *A61F 2002/30904* (2013.01); *A61F 2002/4627* (2013.01); *A61F 2002/4628* (2013.01)

(56) References Cited

U.S. PATENT DOCUMENTS

| | | | |
|---|---|---|---|
| 3,486,505 A | 12/1969 | Morrison |
| 4,309,777 A | 1/1982 | Patil |
| 4,401,112 A | 8/1983 | Rezaian |
| 4,522,200 A | 6/1985 | Stednitz |
| 4,545,374 A | 10/1985 | Jacobson |
| 4,553,273 A | 11/1985 | Wu |
| 4,599,086 A | 7/1986 | Doty |
| 4,636,217 A | 1/1987 | Ogilvie et al. |
| 4,657,550 A | 4/1987 | Daher |
| 4,733,665 A | 3/1988 | Palmaz |
| 4,863,476 A | 9/1989 | Shepperd |
| 4,878,915 A | 11/1989 | Brantigan |
| 4,932,375 A | 6/1990 | Burney |
| 4,932,969 A | 6/1990 | Frey et al. |
| 4,936,851 A | 6/1990 | Fox et al. |
| 4,946,378 A | 8/1990 | Hirayama et al. |
| 5,059,193 A | 10/1991 | Kuslich |
| 5,171,278 A | 12/1992 | Pisharodi |
| 5,192,327 A | 3/1993 | Brantigan |
| 5,236,460 A | 8/1993 | Barber |
| 5,344,252 A | 9/1994 | Kakimoto |
| 5,390,683 A | 2/1995 | Pisharodi |
| 5,425,772 A | 6/1995 | Brantigan |
| 5,484,437 A | 1/1996 | Michelson |
| 5,522,899 A | 6/1996 | Michelson |
| 5,554,191 A | 9/1996 | Lahille et al. |
| 5,562,736 A | 10/1996 | Ray et al. |
| 5,571,190 A | 11/1996 | Ulrich et al. |
| 5,571,192 A | 11/1996 | Schonhoffer |
| 5,593,409 A | 1/1997 | Michelson |
| 5,609,635 A | 3/1997 | Michelson |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,693,100 A | 12/1997 | Pisharodi |
| 5,702,453 A | 12/1997 | Rabbe et al. |
| 5,772,661 A | 6/1998 | Michelson |
| 5,776,197 A | 7/1998 | Rabbe et al. |
| 5,776,199 A | 7/1998 | Michelson |
| 5,782,832 A | 7/1998 | Larsen et al. |
| 5,865,848 A | 2/1999 | Baker |
| 5,888,228 A | 3/1999 | Knothe et al. |
| 5,893,889 A | 4/1999 | Harrington |
| 5,893,890 A | 4/1999 | Pisharodi |
| 5,972,015 A | 10/1999 | Scribner et al. |
| 5,980,522 A | 11/1999 | Koros et al. |
| 6,015,436 A | 1/2000 | Schonhoffer |
| 6,039,761 A | 3/2000 | Li et al. |
| 6,045,579 A | 4/2000 | Hochshuler et al. |
| 6,080,155 A | 6/2000 | Michelson |
| 6,080,193 A | 6/2000 | Hochshuler et al. |
| 6,083,225 A | 7/2000 | Winslow et al. |
| 6,083,228 A | 7/2000 | Michelson |
| 6,090,143 A | 7/2000 | Meriwether et al. |
| 6,093,207 A | 7/2000 | Pisharodi |
| 6,102,949 A | 8/2000 | Biedermann et al. |
| 6,102,950 A | 8/2000 | Vaccaro |
| 6,113,638 A | 9/2000 | Williams et al. |
| 6,117,174 A | 9/2000 | Nolan |
| 6,127,597 A | 10/2000 | Beyar et al. |
| 6,156,037 A | 12/2000 | LeHuec et al. |
| 6,159,244 A | 12/2000 | Suddaby |
| 6,159,245 A | 12/2000 | Meriwether et al. |
| 6,174,334 B1 | 1/2001 | Suddaby |
| 6,176,882 B1 | 1/2001 | Biedermann et al. |
| 6,183,517 B1 | 2/2001 | Suddaby |
| 6,190,414 B1 | 2/2001 | Young et al. |
| 6,193,756 B1 | 2/2001 | Studer et al. |
| 6,193,757 B1 | 2/2001 | Foley et al. |
| 6,206,923 B1 | 3/2001 | Boyd et al. |
| 6,210,412 B1 | 4/2001 | Michelson |
| 6,217,579 B1 | 4/2001 | Koros |
| 6,224,604 B1 | 5/2001 | Suddaby |
| 6,245,107 B1 | 6/2001 | Ferree |
| 6,280,456 B1 | 8/2001 | Scribner et al. |
| 6,287,308 B1 | 9/2001 | Betz et al. |
| 6,302,914 B1 | 10/2001 | Michelson |
| 6,328,738 B1 | 12/2001 | Suddaby |
| 6,332,895 B1 | 12/2001 | Suddaby |
| 6,344,057 B1 | 2/2002 | Rabbe et al. |
| 6,368,351 B1 | 4/2002 | Glenn et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,750 B1 | 6/2002 | Atkinson et al. |
| 6,409,766 B1 | 6/2002 | Brett |
| 6,432,140 B1 | 8/2002 | Lin |
| 6,436,103 B1 | 8/2002 | Suddaby |
| 6,436,140 B1 | 8/2002 | Liu et al. |
| 6,443,989 B1 | 9/2002 | Jackson |
| 6,443,990 B1 | 9/2002 | Aebi et al. |
| 6,447,544 B1 | 9/2002 | Michelson |
| 6,447,547 B1 | 9/2002 | Michelson |
| 6,451,052 B1 | 9/2002 | Burmeister et al. |
| 6,454,806 B1 | 9/2002 | Cohen et al. |
| 6,454,807 B1 | 9/2002 | Jackson |
| 6,478,823 B1 | 11/2002 | Michelson |
| 6,491,724 B1 | 12/2002 | Ferree |
| 6,527,803 B1 | 3/2003 | Crozet et al. |
| D472,632 S | 4/2003 | Anderson |
| D472,633 S | 4/2003 | Anderson |
| 6,562,074 B2 | 5/2003 | Gerbec et al. |
| 6,576,016 B1 | 6/2003 | Hochshuler et al. |
| 6,582,431 B1 | 6/2003 | Ray |
| 6,582,451 B1 | 6/2003 | Marucci et al. |
| 6,582,461 B1 | 6/2003 | Burmeister et al. |
| 6,582,467 B1 | 6/2003 | Teitelbaum et al. |
| 6,592,625 B2 | 7/2003 | Cauthen |
| 6,595,998 B2 | 7/2003 | Johnson et al. |
| 6,610,089 B1 | 8/2003 | Liu et al. |
| 6,626,905 B1 | 9/2003 | Schmiel et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,679,915 B1 | 1/2004 | Cauthen |
| 6,685,742 B1 | 2/2004 | Jackson |
| 6,706,070 B1 * | 3/2004 | Wagner ............... A61F 2/4455 623/17.15 |
| 6,719,796 B2 | 4/2004 | Cohen et al. |
| 6,723,126 B1 | 4/2004 | Berry |
| 6,733,535 B2 | 5/2004 | Michelson |

(56) References Cited

U.S. PATENT DOCUMENTS

| | | |
|---|---|---|
| 6,743,255 B2 | 6/2004 | Ferree |
| 6,758,849 B1 | 7/2004 | Michelson |
| 6,773,460 B2 | 8/2004 | Jackson |
| 6,814,754 B2 | 11/2004 | Greenhalgh |
| 6,814,756 B1 | 11/2004 | Michelson |
| 6,821,298 B1 | 11/2004 | Jackson |
| 6,833,006 B2 | 12/2004 | Foley et al. |
| 6,835,206 B2 | 12/2004 | Jackson |
| 6,837,850 B2 | 1/2005 | Suddaby |
| 6,840,944 B2 | 1/2005 | Suddaby |
| 6,843,804 B2 | 1/2005 | Bryan |
| 6,852,129 B2 | 2/2005 | Gerbec et al. |
| 6,863,673 B2 | 3/2005 | Gerbec et al. |
| 6,875,173 B2 | 4/2005 | Suddaby |
| 6,893,464 B2 | 5/2005 | Kiester |
| 6,902,568 B2 | 6/2005 | Serhan |
| 6,923,810 B1 | 8/2005 | Michelson |
| 6,953,477 B2 | 10/2005 | Berry |
| 6,955,691 B2 | 10/2005 | Chae et al. |
| 6,962,606 B2 | 11/2005 | Michelson |
| 7,018,415 B1 | 3/2006 | McKay |
| 7,066,961 B2 | 6/2006 | Michelson |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,128,760 B2 | 10/2006 | Michelson |
| 7,204,853 B2 | 4/2007 | Gordon et al. |
| 7,214,243 B2 | 5/2007 | Taylor |
| 7,217,291 B2 | 5/2007 | Zucherman et al. |
| 7,220,280 B2 | 5/2007 | Kast et al. |
| D553,742 S | 10/2007 | Park |
| 7,282,063 B2 | 10/2007 | Cohen et al. |
| 7,306,626 B2 | 12/2007 | Whelan |
| 7,311,733 B2 | 12/2007 | Metz-Stavenhagen |
| 7,316,714 B2 | 1/2008 | Gordon et al. |
| 7,326,250 B2 | 2/2008 | Beaurain et al. |
| 7,326,251 B2 | 2/2008 | McCombe et al. |
| 7,331,996 B2 | 2/2008 | Sato et al. |
| 7,503,933 B2 | 3/2009 | Michelson |
| 7,569,074 B2 | 8/2009 | Eisermann et al. |
| 7,618,456 B2 | 11/2009 | Mathieu et al. |
| 7,618,458 B2 | 11/2009 | Biedermann et al. |
| 7,621,951 B2 | 11/2009 | Glenn et al. |
| 7,655,042 B2 | 2/2010 | Foley et al. |
| 7,674,297 B2 | 3/2010 | Falahee |
| 7,678,148 B2 | 3/2010 | Peterman |
| 7,708,778 B2 | 5/2010 | Gordon et al. |
| 7,708,779 B2 | 5/2010 | Edie et al. |
| 7,727,280 B2 | 6/2010 | McLuen |
| 7,731,751 B2 | 6/2010 | Butler et al. |
| 7,731,752 B2 | 6/2010 | Edie et al. |
| 7,753,958 B2 | 7/2010 | Gordon et al. |
| 7,780,732 B2 | 8/2010 | Abernathie |
| 7,789,914 B2 | 9/2010 | Michelson |
| 7,794,501 B2 | 9/2010 | Edie et al. |
| 7,824,445 B2 | 11/2010 | Biro et al. |
| 7,837,734 B2 | 11/2010 | Zucherman et al. |
| 7,850,733 B2 | 12/2010 | Baynham et al. |
| 7,909,830 B2 | 3/2011 | Frigg et al. |
| 7,909,869 B2 | 3/2011 | Gordon et al. |
| 7,985,256 B2 | 7/2011 | Grotz et al. |
| 8,021,430 B2 | 9/2011 | Michelson |
| 8,062,375 B2 | 11/2011 | Glerum et al. |
| 8,070,813 B2 | 12/2011 | Grotz et al. |
| 8,096,994 B2 | 1/2012 | Phan et al. |
| 8,105,358 B2 | 1/2012 | Phan |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,187,331 B2 | 5/2012 | Strohkirch, Jr. et al. |
| D664,252 S | 7/2012 | Weiland et al. |
| 8,257,440 B2 | 9/2012 | Gordon et al. |
| 8,267,939 B2 | 9/2012 | Cipoletti et al. |
| 8,273,124 B2 | 9/2012 | Renganath et al. |
| 8,273,126 B2 | 9/2012 | Lindner |
| 8,303,662 B2 | 11/2012 | Landry et al. |
| 8,303,663 B2 | 11/2012 | Jimenez et al. |
| 8,328,818 B1 | 12/2012 | Seifert et al. |
| 8,337,558 B2 | 12/2012 | Lindner |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,568,481 B2 | 10/2013 | Olmos et al. |
| 9,962,270 B2 * | 5/2018 | Alheidt ............... A61F 2/4611 |
| 2001/0032020 A1 | 10/2001 | Besselink |
| 2002/0045945 A1 | 4/2002 | Liu et al. |
| 2002/0052656 A1 | 5/2002 | Michelson |
| 2002/0068974 A1 | 6/2002 | Kuslich et al. |
| 2002/0068977 A1 | 6/2002 | Jackson |
| 2002/0082696 A1 | 6/2002 | Harms et al. |
| 2002/0128716 A1 | 9/2002 | Cohen et al. |
| 2002/0138146 A1 | 9/2002 | Jackson |
| 2003/0004575 A1 | 1/2003 | Erickson |
| 2003/0040798 A1 | 2/2003 | Michelson |
| 2003/0065396 A1 | 4/2003 | Michelson |
| 2003/0135279 A1 | 7/2003 | Michelson |
| 2003/0149482 A1 | 8/2003 | Michelson |
| 2003/0171813 A1 | 9/2003 | Kiester |
| 2003/0195630 A1 | 10/2003 | Ferree |
| 2003/0208263 A1 | 11/2003 | Burmeister et al. |
| 2003/0208270 A9 | 11/2003 | Michelson |
| 2003/0208272 A1 | 11/2003 | Crozet et al. |
| 2003/0208275 A1 | 11/2003 | Michelson |
| 2003/0220650 A1 | 11/2003 | Major et al. |
| 2003/0236520 A1 | 12/2003 | Lim et al. |
| 2004/0010312 A1 | 1/2004 | Enayati |
| 2004/0010315 A1 | 1/2004 | Song |
| 2004/0024460 A1 | 2/2004 | Ferree |
| 2004/0024463 A1 | 2/2004 | Thomas, et al. |
| 2004/0030387 A1 | 2/2004 | Landry et al. |
| 2004/0044411 A1 | 3/2004 | Suddaby |
| 2004/0078080 A1 | 4/2004 | Thramann et al. |
| 2004/0087947 A1 | 5/2004 | Lim et al. |
| 2004/0087948 A1 | 5/2004 | Suddaby |
| 2004/0102774 A1 | 5/2004 | Trieu |
| 2004/0153156 A1 | 8/2004 | Cohen et al. |
| 2004/0199252 A1 | 10/2004 | Sears et al. |
| 2004/0215342 A1 | 10/2004 | Suddaby |
| 2004/0225360 A1 | 11/2004 | Malone |
| 2004/0243240 A1 | 12/2004 | Beaurain et al. |
| 2004/0254643 A1 | 12/2004 | Jackson |
| 2004/0254644 A1 | 12/2004 | Taylor |
| 2005/0004673 A1 | 1/2005 | Kluger |
| 2005/0015149 A1 | 1/2005 | Michelson |
| 2005/0015150 A1 | 1/2005 | Lee |
| 2005/0027358 A1 | 2/2005 | Suddaby |
| 2005/0038512 A1 | 2/2005 | Michelson |
| 2005/0049590 A1 | 3/2005 | Alleyne et al. |
| 2005/0060036 A1 | 3/2005 | Schultz et al. |
| 2005/0070911 A1 | 3/2005 | Carrison et al. |
| 2005/0071007 A1 | 3/2005 | Malek |
| 2005/0113920 A1 | 5/2005 | Foley et al. |
| 2005/0273171 A1 | 12/2005 | Gordon et al. |
| 2005/0278026 A1 | 12/2005 | Gordon et al. |
| 2006/0022180 A1 | 2/2006 | Selness |
| 2006/0064169 A1 | 3/2006 | Ferree |
| 2006/0116767 A1 | 6/2006 | Magerl et al. |
| 2006/0122701 A1 | 6/2006 | Kiester |
| 2006/0129244 A1 | 6/2006 | Ensign |
| 2006/0149385 A1 | 7/2006 | McKay |
| 2006/0206207 A1 | 9/2006 | Dryer et al. |
| 2006/0224241 A1 | 10/2006 | Butler et al. |
| 2006/0241643 A1 | 10/2006 | Lim et al. |
| 2006/0241764 A1 | 10/2006 | Michelson |
| 2006/0247770 A1 | 11/2006 | Peterman |
| 2006/0253201 A1 | 11/2006 | McLuen |
| 2008/0058931 A1 | 3/2008 | White et al. |

(56) References Cited

U.S. PATENT DOCUMENTS

| | | |
|---|---|---|
| 2008/0071279 A1 | 3/2008 | Bandeira et al. |
| 2008/0082173 A1 | 4/2008 | Delurio et al. |
| 2008/0140207 A1* | 6/2008 | Olmos .................. A61F 2/4611 623/17.16 |
| 2009/0222100 A1 | 9/2009 | Cipoletti et al. |
| 2010/0017965 A1 | 1/2010 | Barthelt |
| 2010/0049325 A1 | 2/2010 | Biedermann et al. |
| 2010/0145455 A1 | 6/2010 | Simpson et al. |
| 2010/0211176 A1 | 8/2010 | Greenhalgh |
| 2010/0280616 A1 | 11/2010 | Frasier |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0331985 A1 | 12/2010 | Gordon et al. |
| 2011/0130838 A1 | 6/2011 | Morgenstern Lopez |
| 2011/0160861 A1* | 6/2011 | Jimenez ............. A61B 17/7065 623/17.16 |
| 2011/0172774 A1 | 7/2011 | Varela |
| 2012/0035729 A1 | 2/2012 | Glerum et al. |
| 2012/0071982 A1 | 3/2012 | Michelson |
| 2012/0191194 A1 | 7/2012 | Olmos et al. |
| 2012/0290094 A1 | 11/2012 | Lim et al. |
| 2012/0310349 A1 | 12/2012 | Gordon et al. |
| 2012/0316652 A1 | 12/2012 | Renganath et al. |

FOREIGN PATENT DOCUMENTS

| | | |
|---|---|---|
| DE | 102005022920 A1 | 11/2006 |
| EP | 0260044 A1 | 3/1988 |
| EP | 0269175 A2 | 6/1988 |
| EP | 0566807 A1 | 10/1993 |
| EP | 0637439 A1 | 2/1995 |
| EP | 0664994 A1 | 8/1995 |
| EP | 0669114 A1 | 8/1995 |
| EP | 0734702 A1 | 10/1996 |
| EP | 1293180 A1 | 3/2003 |
| GB | 2083754 A | 3/1982 |
| GB | 2219060 A | 11/1989 |
| JP | 62164458 A | 7/1987 |
| JP | 63158045 A | 7/1988 |
| JP | 5208029 A | 8/1993 |
| WO | 9000037 A1 | 1/1990 |
| WO | 9428824 A2 | 12/1994 |
| WO | 9525485 A1 | 9/1995 |
| WO | 9532673 A1 | 12/1995 |
| WO | 9614809 A1 | 5/1996 |
| WO | 9627321 A2 | 9/1996 |
| WO | 9627345 A2 | 9/1996 |
| WO | 9639988 A2 | 12/1996 |
| WO | 9640015 A1 | 12/1996 |
| WO | 9640016 A2 | 12/1996 |
| WO | 9640019 A1 | 12/1996 |
| WO | 9640020 A1 | 12/1996 |
| WO | 9913806 A1 | 3/1999 |
| WO | 2002009626 A1 | 2/2002 |
| WO | 2003003951 A1 | 1/2003 |
| WO | 03092507 A2 | 11/2003 |
| WO | 2004047691 A1 | 6/2004 |
| WO | 2004080356 A2 | 9/2004 |
| WO | 2006034436 A2 | 3/2006 |
| WO | 2006037013 A1 | 4/2006 |
| WO | 2006042334 A2 | 4/2006 |
| WO | 2006050500 A2 | 5/2006 |
| WO | 2006068682 A1 | 6/2006 |
| WO | 2006116760 A2 | 11/2006 |
| WO | 2006116761 A2 | 11/2006 |
| WO | 2007009107 A2 | 1/2007 |
| WO | 2007041665 A2 | 4/2007 |
| WO | 2008070863 A2 | 6/2008 |
| WO | 2010148112 A1 | 12/2010 |
| WO | 2011047230 A1 | 4/2011 |

OTHER PUBLICATIONS

Milton, AIPLA quarterly Journal, vol. 34, No. 3, p. 333-358, Summer 2006.
WAVE Plif Cage, "Product Information: Tthe Expandable Lumbar Cage", Advanced Medical Technologies AG (date unkown.).
Supplementary European Search Report for Application No. EP 12823945 dated Sep. 26, 2014.
Extended European Search Report for Application No. EP16189450 dated Nov. 16, 2016.

* cited by examiner

EXPANDABLE IMPLANT

CROSS-REFERENCE TO RELATED APPLICATIONS

The present application is a continuation of U.S. application Ser. No. 15/091,058, filed on Apr. 5, 2016, which is a continuation of U.S. application Ser. No. 13/587,205, filed on Aug. 16, 2012, which claims the benefit of the filing date of U.S. Provisional Patent Application No. 61/523,981 filed Aug. 16, 2011, the disclosures of which are hereby incorporated herein by reference in their entirety.

FIELD OF THE INVENTION

The present invention relates to expandable implants and tools for the insertion of such implants. More particularly, the invention pertains to an expandable spinal implant having opposed plates, which are expandable via wedge members and ramped surfaces included on the plates. An insertion instrument used for implantation of the implant, and methods of utilizing the same, are also disclosed.

BACKGROUND OF THE INVENTION

Common degenerative spinal diseases, such as chronic degeneration of an intervertebral disc of the spine, may result in substantial pain and discomfort for a patient. Frequently, diseases of this type need to be treated through surgical intervention, which may include replacing the affected disc(s) and potentially fusing the associated vertebrae through the use of an implant or other like device. In particular applications, adjacent vertebral bodies may be fused via an implant, through screw arrangements, and/or by using bone graft material to secure the vertebrae in a fixed state. Exemplary indications for such devices include, but are not limited to, spinal stenosis, degenerative disc disease with a loss of disc height, disc herniation, spondylolisthesis, retrolisthesis, and disogenic back pain.

In replacing a diseased intervertebral disc(s) and effecting fusion, it may also be necessary to ensure that proper spacing is maintained between the vertebral bodies. Stated differently, once the implant or other like device is situated between adjacent vertebrae, the implant or device should adequately recreate the spacing previously maintained via the excised intervertebral disc (e.g., in its natural condition). Various expandable implants have been designed for this purpose. As such, it is possible for a surgeon to adjust the height of particular intervertebral implants to intra-operatively tailor the implant height to match the natural spacing between vertebrae, or any desired implant height. This may reduce the number of different implants needed to accommodate the varying anatomical confines of different patients.

Certain components of expandable implants, however, such as plates forming a part thereof, may be subject to torsional forces and/or compressive forces upon distraction or implantation. In some cases, the expansion mechanism of the implant may serve to keep the plates in alignment with one another to counteract these forces. In addition, rods or support bars have been used to inhibit the effect of torsional forces acting on the plates.

Although several versions of expandable intervertebral implants are known, the need for an improved expandable implant, which is expandable in situ and provides structures for keeping plates of the expandable implant in alignment with one another remains.

BRIEF SUMMARY OF THE INVENTION

A first aspect of the invention provides an expandable intervertebral implant having top and bottom plates with inner and outer surfaces, the inner surfaces facing each other and each having a ramp surface and a recess disposed adjacent the ramp surface. An actuator is also situated between the inner surfaces of the top and bottom plates, and first and second expansion members are coupled to the actuator and located between the inner surfaces of the top and bottom plates. In some cases, the first and second expansion members each have at least one vertical projection extending outwardly therefrom. Rotation of the actuator in opposing directions may cause the first and second expansion members to move toward and away from one another along a longitudinal axis of the actuator, resulting in movement of the top and bottom plates toward and away from one another along a vertical axis perpendicular to the longitudinal axis. The at least one vertical projection of the first and second expansion members may also be received and guided at least partially within one of the recesses adjacent the ramp surfaces of the top or bottom plates while such plates move along the vertical axis.

In embodiments of the first aspect, the first and second expansion members may also each include at least one lateral projection received within a corresponding lateral slot situated adjacent the ramp surface of each of the top and bottom plates. The actuator may also include first and second threaded portions, the first and second threaded portions having oppositely facing threads configured to engage threads of the first and second expansion members, such that when the actuator is rotated, the first and second expansion members move along the longitudinal axis of the actuator in opposite directions.

In a second aspect of the invention, an expandable intervertebral implant is provided in which the implant comprises top and bottom plates having inner and outer surfaces, the inner surfaces facing each other and each having a ramp surface. An actuator may also be situated between the inner surfaces of the top and bottom plates, and first and second expansion members may be coupled to the actuator and located between the inner surfaces of the top and bottom plates, the first and second expansion members each having a horizontal portion with at least one projection extending outward therefrom. Rotation of the actuator in opposing directions may cause the horizontal portion of the first and second expansion members to translate along the ramp surfaces toward and away from one another along a longitudinal axis of the actuator, resulting in movement of the top and bottom plates toward and away from one another along a vertical axis perpendicular to the longitudinal axis, the projections of the horizontal portions being received within at least one lateral slot situated adjacent each ramp surface as the top and bottom plates move along the vertical axis.

In some embodiments of the second aspect, the inner surfaces of the top and bottom plates each include a recess adjacent the respective ramp surface, and the first and second expansion members each include a vertical portion adapted to translate within the recesses during movement of the top and bottom plates along the vertical axis. Other embodiments include the horizontal portion of the first and second expansion members having at least a first and second projection extending therefrom, the first projection being received within a lateral slot situated adjacent the ramp surface of the top plate, and the second projection being received within a lateral slot situated adjacent the ramp surface of the bottom plate. The lateral slots may also each include a terminal portion, and the first and second projections may be adapted to interact with the terminal portion to prevent movement of the first and second expansion members away from one another.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which:

FIG. 13A is a perspective view of an alternate expandable implant according to one embodiment of the present invention, while

DETAILED DESCRIPTION

Figure 1A:
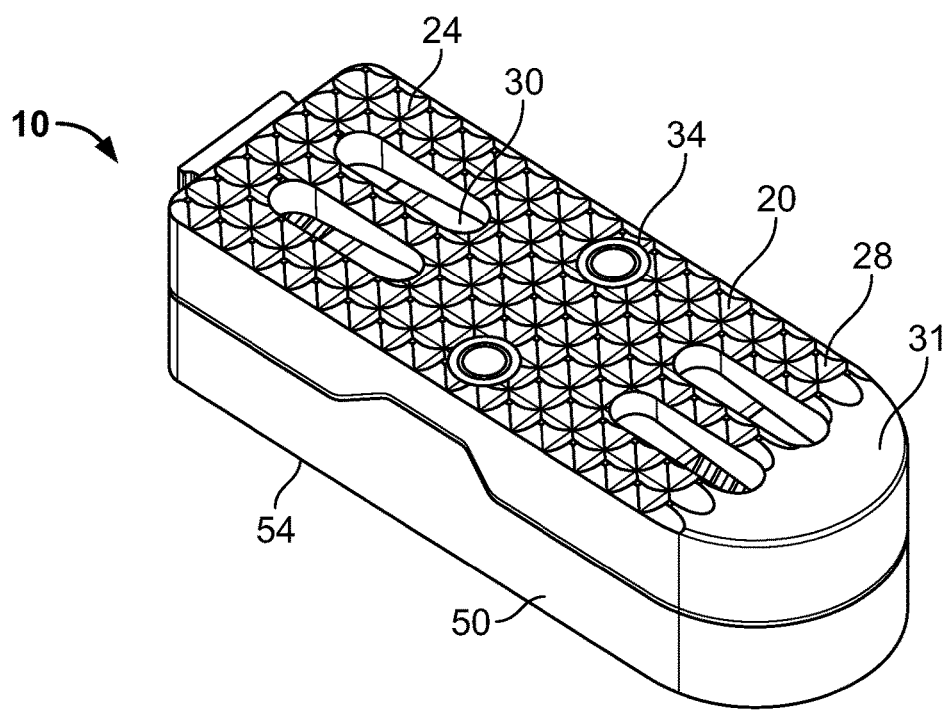
FIGS. 1A-B are perspective views of an expandable implant according to one embodiment of the present invention, with FIG. 1A showing the implant in collapsed form, and FIG. 1B showing the implant expanded.

In describing the preferred embodiments of the invention(s) illustrated and to be described with respect to the drawings, specific terminology will be used for the sake of clarity. However, the invention(s) is not intended to be limited to any specific terms used herein, and it is to be understood that each specific term includes all technical equivalents, which operate in a similar manner to accomplish a similar purpose. For instance, while the terms "top" and "bottom" are used herein, such terms are utilized merely for convenience, and it is contemplated that the various implants disclosed may be situated in several orientations, such that these spatial terms may not apply (e.g., they may be reversed).

Referring to FIGS. 1A-3B, there is shown one embodiment of an expandable implant 10, which in some cases may be used as an intervertebral implant, the expandable implant 10 having, generally: (1) top and bottom plates 20, 50 situated in opposition to one another; (2) a rod or axle 80 arranged between the top and bottom plates 20, 50; and (3) expansion members 100, 102 for contacting angled surfaces 22, 52 on top and bottom plates 20, 50, respectively, and for expanding the implant 10 (e.g., in situ). In use, implant 10 may be inserted between adjacent vertebral bodies and expanded through use of an instrument, such as instrument 120 shown in FIGS. 4A-B, for example. This system provides a surgeon, nurse, or other skilled practitioner (hereinafter "the user") with an improved expandable implant 10 for use in interventional procedures designed to combat various degenerative disorders, for example.

Figure 1B:
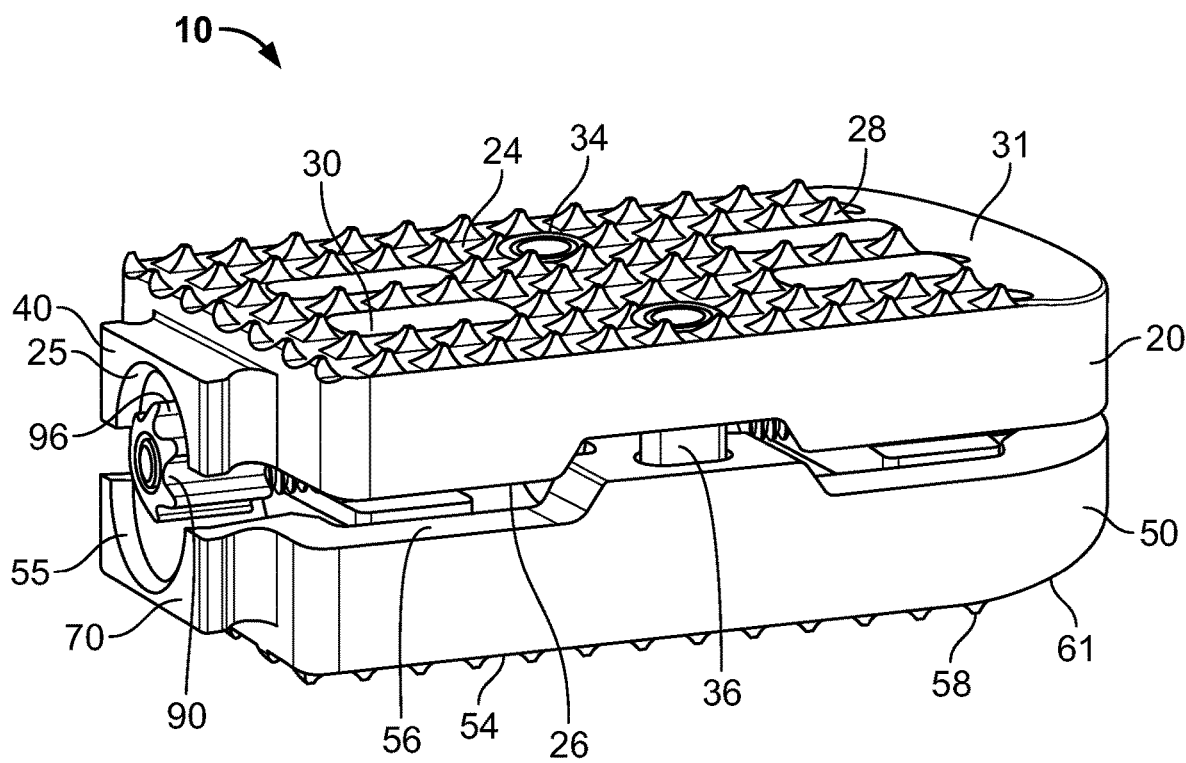
Figure 2A:
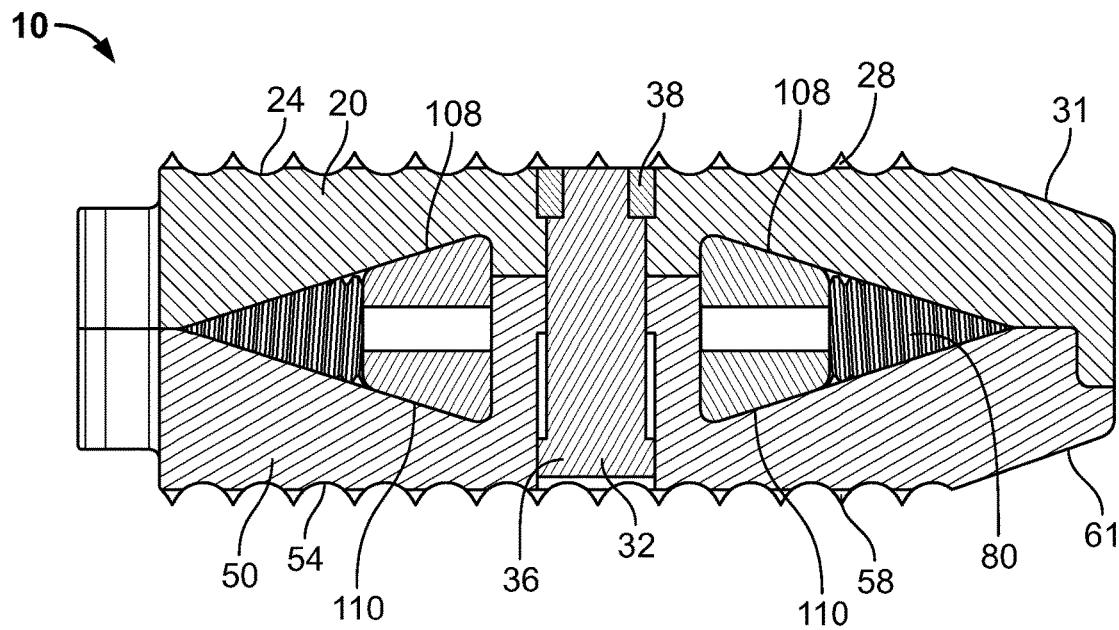
FIGS. 2A-B are cross-sectional views of the implant of FIGS. 1A-1B.
Figure 2B:
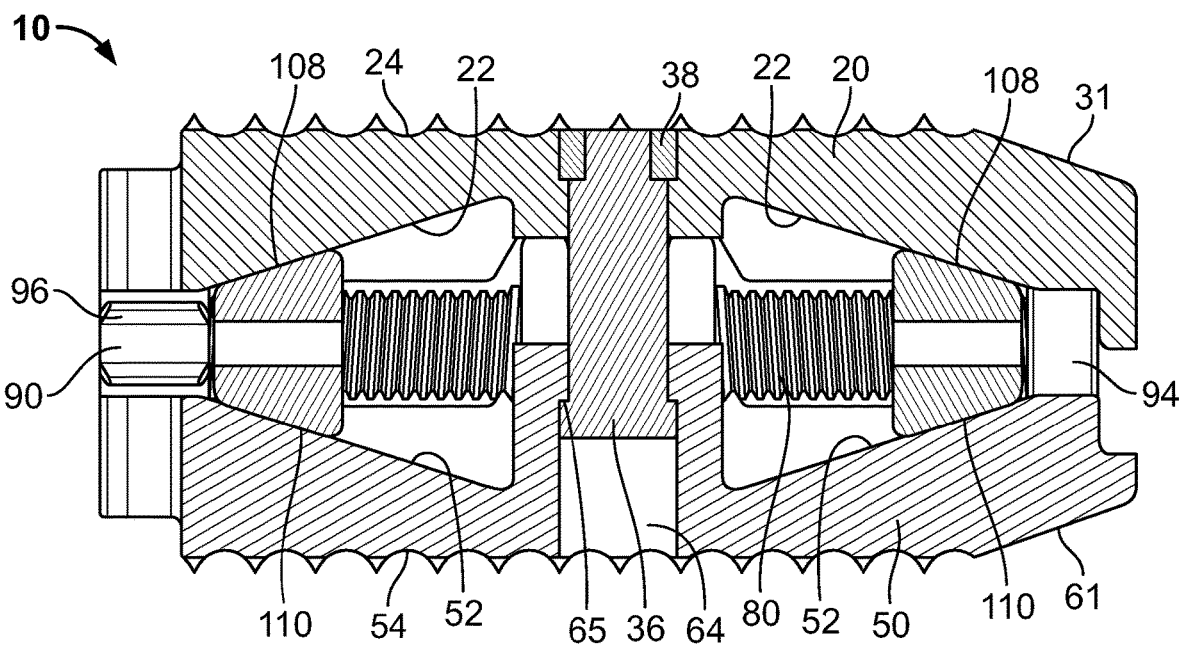

Referring to FIGS. 1A-B, top and bottom plates 20, 50 may include outer bone-contacting surfaces 24, 54 and inner surfaces 26, 56 opposed to the outer surfaces 24, 54. In one embodiment, outer bone-contacting surfaces 24, 54 may include teeth, notches, serrations, keels, or other bone-penetrating features 28, 58 for engaging bone during use. An end of top and bottom plates 20, 50 may also be tapered 31, 61 for facilitating implantation of implant 10, in one embodiment. Top plate 20 may also include, as shown in FIG. 1A, multiple elongate apertures 30 for facilitating bone in-growth or for receiving other biocompatible materials, for example. In some cases, top plate 20 may include four elongate apertures 30, while bottom plate 50 may only include two, as reflected in FIGS. 3A-B, respectively. A separate set of apertures 34, 64 may also be formed in plates 20, 50 for receiving a post(s) 36 and nut(s) 38 construct, as shown in FIGS. 2A-B. In one embodiment, apertures 34 in top plate 20 may be generally thin in comparison to the elongate nature of apertures 64 in bottom plate 50, thereby guiding and facilitating movement of posts 36 in apertures 64. Each of plates 20, 50 may also include a projection 40, 70, which in one embodiment may be dovetail-shaped.

Figure 3A:
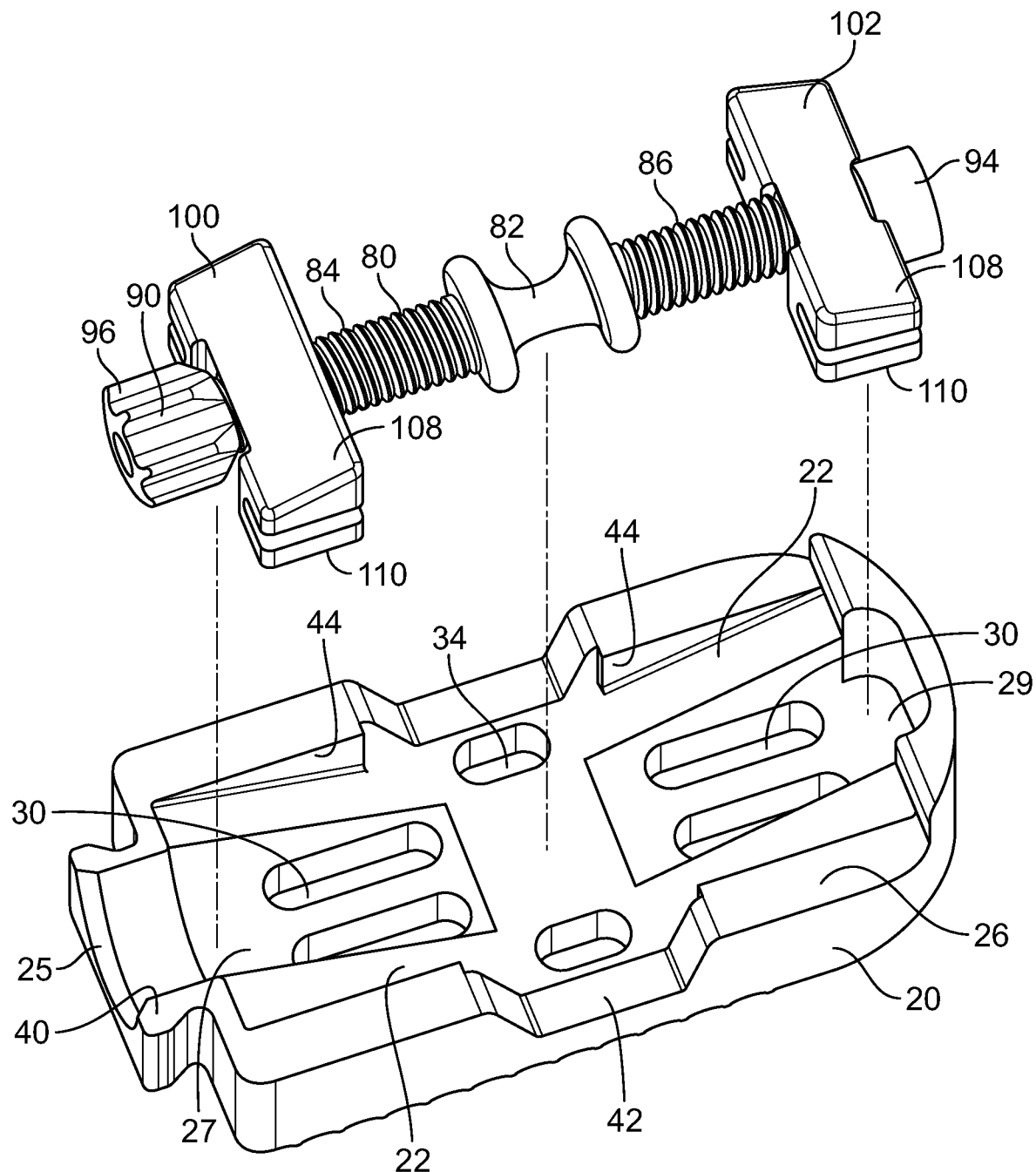
FIGS. 3A-B are exposed views of the top and bottom plates, respectively, of the implant of FIGS. 1A-1B, with the distraction mechanism shown alongside the relevant plate.
Figure 3B:
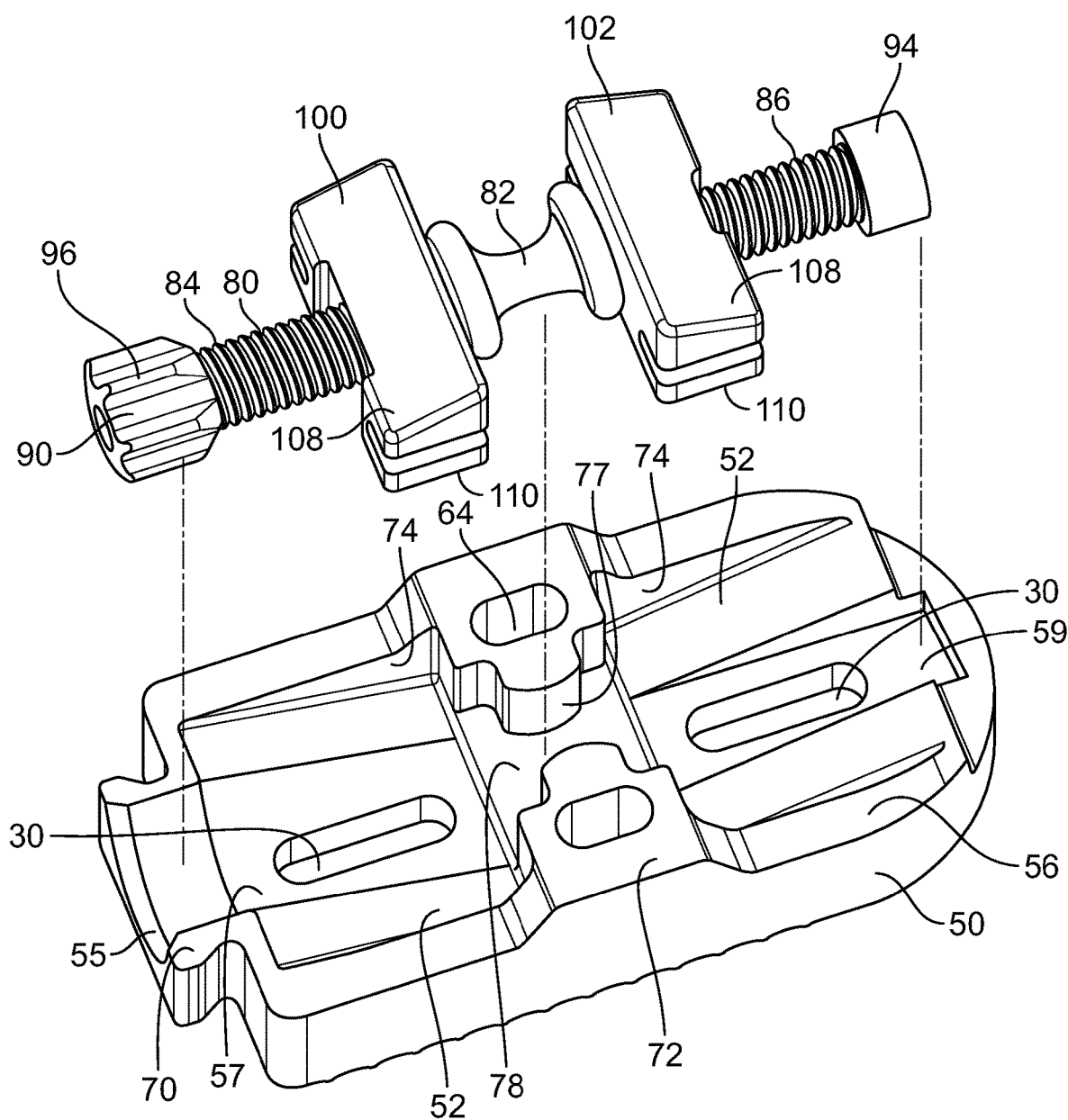

Inner surfaces 26, 56 of top and bottom plates 20, 50, as shown, respectively, in FIGS. 3A-3B may each include angled surfaces 22, 52 on either side of a center of the plate 20, 50. In particular, referring to FIG. 3B, bottom plate 50 may include a raised center 72 having apertures 64, and on either side of center 72 may be an angled surface(s) 52. Such surfaces 52 may also be angled in a direction extending from respective ends of plate 50 to raised center 72. Likewise, referring to FIG. 3A, top plate 20 may include a recessed center 42 having apertures 34, and on either side of recessed center 42 may be an angled surface(s) 22. Further, such surfaces 22 may be angled in a direction extending from respective ends of plate 20 to recessed center 42. Thus, angled surfaces 22, 52 of plates 20, 50 may converge towards one another, in one embodiment, as shown in FIGS. 3A-B.

Angled surfaces 22, 52 of plates 20, 50 may also be bounded by adjacent side walls 44, 74 for guiding expansion members 100, 102, as described in detail below. Further: (1) raised center portion 72 may include a cutout 78 for accommodating an hourglass-shaped structure 82; (2) one end of each plate 20, 50 may include a semi-cylindrical cutout 29, 59 for accommodating part of axle 80; and (3) dovetail-shaped projections 40, 70 may each include a semi-cylindrical opening 25, 55 for receiving another portion of axle 80. Inner surfaces 26, 56 of plates 20, 50 may also include a channel 27, 57 for housing axle 80.

Referring still to FIGS. 3A-B, axle 80 may be situated between plates 20, 50, and may include an hourglass-shaped member 82. First and second threaded sections 84, 86 may also be arranged on opposite sides of hourglass-shaped member 82, such sections 84, 86 having opposed right and left-handed threading. In other words, as an example, threaded section 84 may be situated on one side of hourglass-shaped member 82 and include left-hand threads, while threaded section 86 may be positioned on an opposing side of hourglass-shaped member 82 and include right-hand threads.

Expansion members 100, 102 may also be situated on axle 80, such members 100, 102 each including an internally-threaded bore (not shown) for receiving one of threaded sections 84, 86. In some embodiments, expansion members 100, 102 may include top and bottom surfaces 108, 110 angled in opposition to angled surfaces 22, 52 and in opposition to one another. Stated differently, top surfaces 108 of expansion members 100, 102 may be angled to seat flush with angled surfaces 22 of top plate 20, while bottom surfaces 110 of expansion members 100, 102 may be angled to seat flush with angled surfaces 52 of bottom plate 50, as shown in detail in FIGS. 2A-B. As such, top and bottom surfaces 108, 110 of expansion members 100, 102 may form a wedge.

At one end of axle 80 there may also be an engagement nut 90, while at an opposing end of axle 80 may be stop nut 94. Engagement and/or stop nuts 90, 94 may either be separate components threaded onto axle 80, or, in some embodiments, may be unitarily formed with axle 80. Engagement nut 90 includes ridges or serrations 96 on an exterior surface thereof for attaching with a portion of instrument 120, and stop nut 94 comprises a smooth and enlarged exterior surface for interacting with a portion of expansion members 100, 102. In one embodiment, ridges 96 on engagement nut 90 may form a Torx structure.

To construct implant 10, top and bottom plates 20, 50 may first be situated in opposition to one another with inner surfaces 26, 56 facing towards each other. Axle 80, previously assembled to include expansion members 100, 102, and engagement 90 and stop 94 nuts, may also be situated between plates 20, 50 and within channels 27, 57. In this configuration, top surfaces 108 of expansion members 100, 102 may engage with angled surfaces 22 of top plate 20, and bottom surfaces 110 of expansion members 100, 102 may engage with angled surfaces 52 of bottom plate 50, as shown in FIGS. 2A-B. Further, engagement nut 90 may be surrounded by semi-cylindrical openings 25, 55 of dovetail-shaped projections 40, 70, and stop nut 94 by semi-cylindrical openings 29, 59. An end of posts 36, which in some cases includes an enlarged head 32, may also be accommodated within apertures 64 in bottom plate 50, and a stop surface 65 within each aperture 64 may prevent passage of head 32 completely through the aperture 64 (FIG. 2B). An opposing end of posts 36, which in some instances includes threading, may also be situated within apertures 34 in top plate 20 and be engaged with nuts 38 housed in apertures 34. As such, plates 20, 50 may be connected together via posts 36, which may allow expansion of implant 10 through movement of heads 32 within apertures 64 in bottom plate 50, as shown in detail in the progression between FIGS. 2A-B.

With plates 20, 50 connected together as described above, and in an unexpanded state (FIGS. 1A, 2A), raised center section 72 of bottom plate 50 may be accommodated within recessed center section 42 of top plate 20, and a perimeter of inner surfaces 26, 56 may be in contact with one another. Further, hourglass-shaped member 82 of axle 80 may be situated within the cutout 78 in bottom plate 50. What is more, protrusions 77 extending into cutout 78 may engage a portion of hourglass-shaped member 82 to stabilize axle 80 along a longitudinal axis of plates 20, 50 (FIG. 3B).

In this orientation, rotation of axle 80 in one direction may cause corresponding outward movement of expansion members 100, 102 (e.g., towards the ends of axle 80), and rotation in another opposite direction may cause inward movement of expansion members 100, 102 (e.g., towards hourglass-shaped member 82). Such movement of expansion members 100, 102 may also interact with angled surface 22, 52 on plates 20, 50 to cause corresponding expansion or collapse of implant 10 (e.g., within an intervertebral disc space), as shown in FIGS. 2A-B. In particular, movement of expansion members 100, 102 generally towards the ends of axle 80 may cause such members 100, 102 to ride up angled surfaces 22, 52 on plates 20, 50 and thereby cause expansion of implant 10. Further, with top and bottom surfaces 108, 110 of expansion members 100, 102 being angled in the manner discussed above, the movement of plates 20, 50 may be generally uniform. In other words, were respective planes drawn along outer bone-contacting surfaces 24, 54 of plates 20, 50, upon expansion of implant 10, such planes would remain in generally the same orientation with respect to one another (i.e., due to top and bottom surfaces 108, 110 of expansion members 100, 102 being set flush against angled surfaces 22, 52). It is also contemplated that, in one embodiment, the aforementioned planes (and thus outer bone-contacting surfaces 24, 54) may be arranged at lordotic angles to one another. This may appropriately accommodate lordosis of adjacent vertebral bodies, if present. Such lordotic angles may also be maintained upon expansion of implant 10.

During the above-described expansion of implant 10, axle 80 may rotate within channels 27, 57, and particularly: (1) hourglass-shaped member 82 may rotate within cutout 78; (2) engagement nut 90 within semi-circular openings 25, 55; and (3) stop nut 94 within semi-circular openings 29, 59. Further, as noted above, due to the reverse threading of threaded sections 84, 86, upon rotation of axle 80, expansion members 100, 102 may move towards or away from one another (i.e., in opposing directions). Such movement of expansion members 100, 102 may also be limited by engagement 90 and stop 94 nuts, and hourglass-shaped member 82. In addition, during expansion of implant 10, expansion members 100, 102 may be stabilized via side walls 44, 74 of inner surfaces 26, 76, and posts 36 may limit and/or prevent over-expansion of implant 10. Indeed, as expansion members 100, 102 move plates 20, 50 apart, the head 32 of posts 36 may slide within elongate apertures 64 in plate 50 until such a point as head 32 contacts stop surface 65, as shown in FIG. 2B. Thus, posts 36 may act to prevent over distraction of implant 10. Further, posts 36 may also operate to stabilize implant 10 upon expansion, since sections of posts 36 are engaged with both top and bottom plates 20, 50 during expansion. In other words, posts 36 may serve to provide torsional and/or compressive stability to plates 20, 50 in one embodiment.

As such, in use, implant 10 may be inserted into the intervertebral disc space of a patient, with outer bone-contacting surfaces 24, 54 engaging adjacent vertebrae, and such implant 10 may be expanded in the manner described above. Further details pertaining to this method of expansion, and the insertion of the implant 10 within an intervertebral space, are set forth in subsequent sections.

Figure 4A:
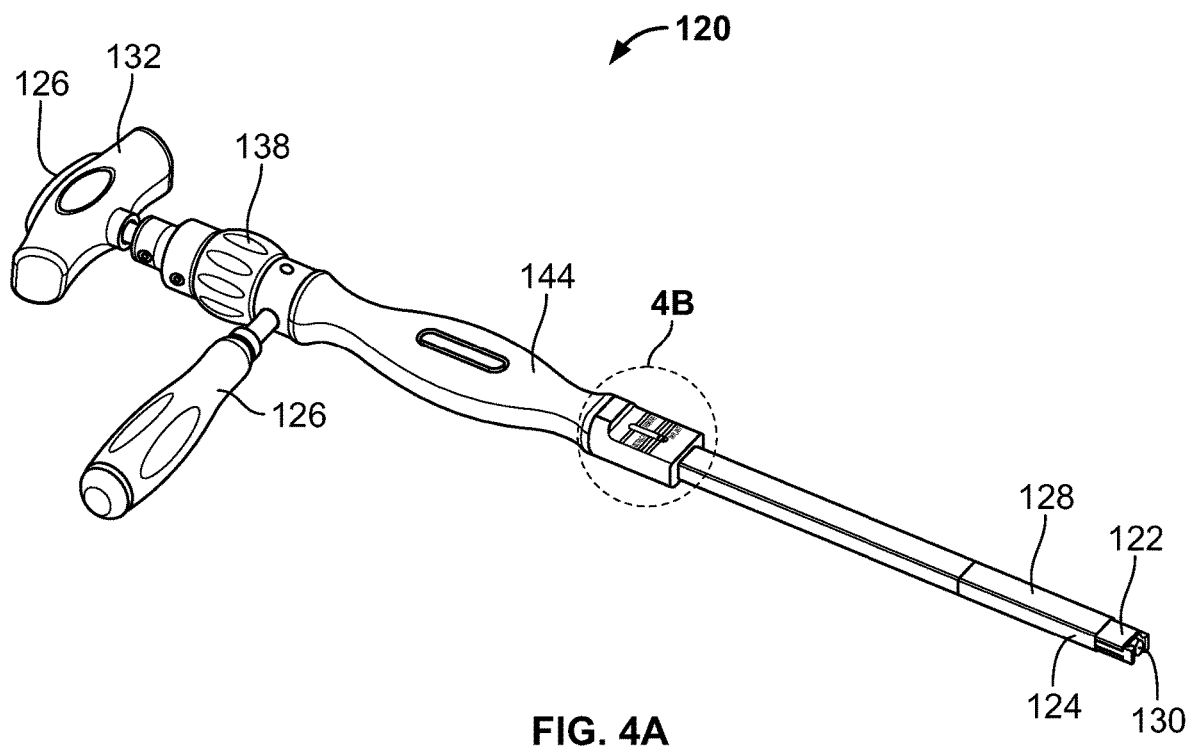
FIGS. 4A-B are perspective views of an instrument used for implantation, removal, and distraction of an expandable implant.
Figure 4B:
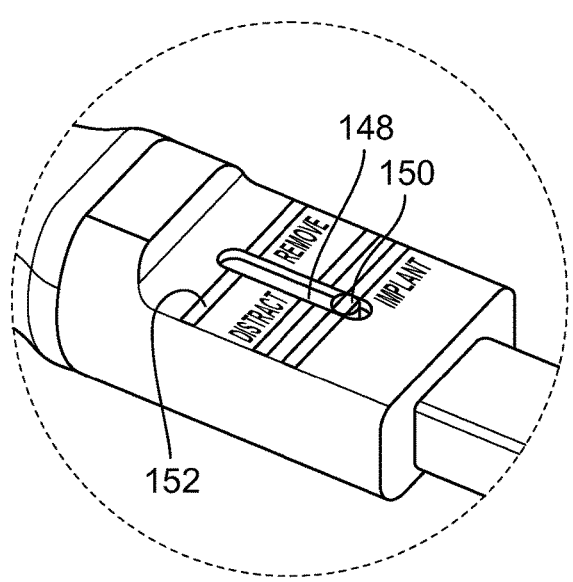

Referring to FIGS. 4A-B, there is shown an instrument 120 engageable with the aforementioned implant 10, and usable to place implant 10 at the treatment site (e.g., within the intervertebral disc space). Instrument 120 may generally include: (1) a shaft 122 with a sleeve 128 overlying the shaft 122; (2) distal 124 and proximal 126 ends; (3) a socket 130 for engaging with engagement nut 90; and (4) a rotatable handle 132 connected to socket 130, such that rotation of handle 132 may cause rotation of socket 130 and expansion of implant 10 (e.g., when instrument 120 is engaged with engagement nut 90). Distal end 124 of instrument 120 may also include fingers 134, 136 that are engageable with dovetail-shaped projections 40, 70, and may be actuated via a knob 138 situated adjacent proximal end 126 of instrument 120. Thus, instrument 120 may provide a useful tool for a user in the insertion and/or expansion of implant 10, as detailed more fully below.

As shown in FIG. 4A, handle 132 of instrument 120 may be connected to a rod (not shown) extending generally within and along shaft 122 of instrument 120. The rod may extend to distal end 124 of instrument 120 and may terminate in socket 130, which in one embodiment may be configured to engage with engagement nut 90. In some instances, socket 130 may be a Torx-type socket for engaging with an engagement nut 90 having Torx structure. A separate handle 142 may also be provided adjacent proximal end 126, such handle 142 extending generally outward from instrument 120. Instrument 120 may also include a grip 144. Handle 142 and grip 144 may allow the user to effectively grasp instrument 120 during insertion of implant 10 into the intervertebral disc space.

FIG. 4A further depicts a knob 138 adjacent proximal end 126 that is rotatable about a longitudinal axis of shaft 122. An interior of knob 138 may include internal threading for cooperating with an actuator (not shown) connected to sleeve 128. The threading within knob 138 may be configured such that, upon rotation of knob 138 in one direction, the actuator and sleeve 128 may move longitudinally towards distal end 124; and, upon rotation of knob 138 in an opposing direction, the actuator and sleeve 128 may move longitudinally towards proximal end 126.

A viewing window 148 may also be provided with instrument 120, as shown in close-up in FIG. 4B, for indicating to a user of instrument 120 the particular mode in which instrument 120 is situated (e.g., "implant" mode, "distract" mode, or "remove" mode). An indicator 150 may be housed within viewing window 148, and a series of markings 152 may also be situated adjacent the window 148. Further, in one embodiment, wording or other information may be provided proximate viewing window 148 and markings 152 to inform a user of the mode in which instrument 120 is placed.

Figure 5A:
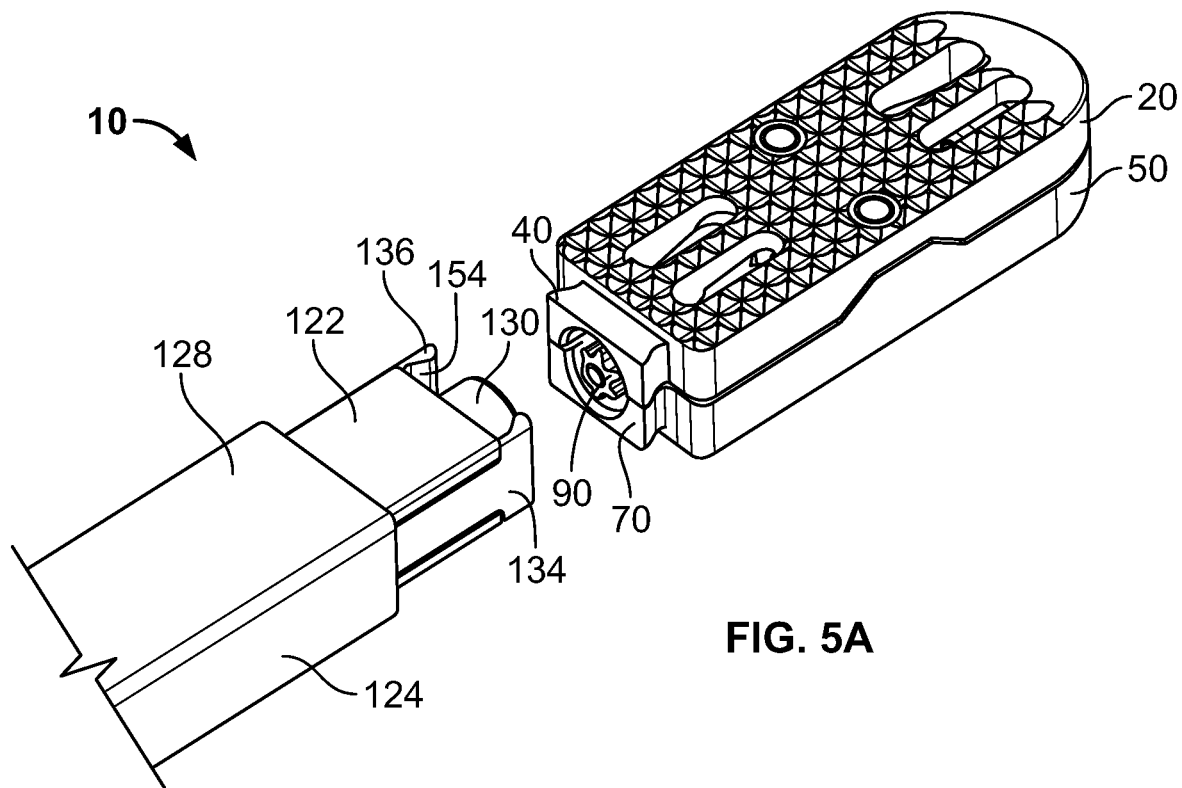
FIGS. 5A-B are perspective views of the instrument of FIGS. 4A-B, in which the instrument is being attached to the implant.
Figure 5B:
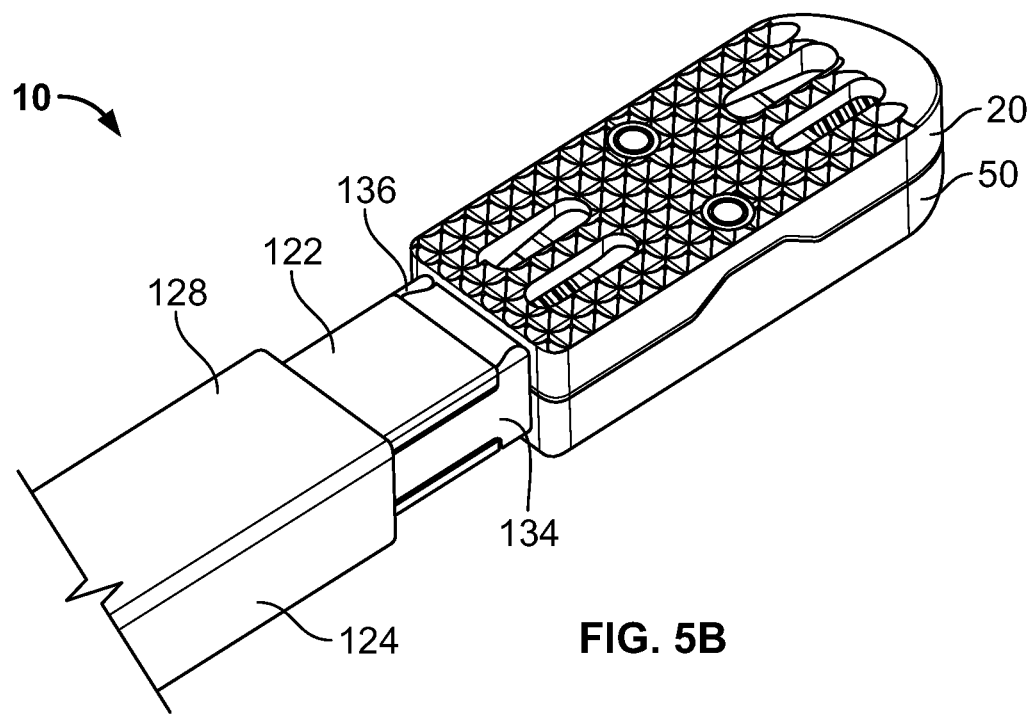

Referring to FIGS. 5A-B, distal end 124 of shaft 122 of instrument 120 may be provided with resilient fingers 134, 136 running along opposing sides of shaft 122, and positioned within channels (not shown) in shaft 122. Each finger 134, 136 may include an end having generally angled surfaces 154 for engaging with projections 40, 70 on implant 10. In one embodiment, fingers 134, 136 may be shaped to conform to the dovetail shape of projections 40, 70.

In use, referring still to FIGS. 5A-B, distal end 124 of instrument 120 may be positioned adjacent dovetail-shaped projections 40, 70 of implant 10 so that socket 130 of instrument 120 may be attached to engagement nut 90. Specifically, as shown in the progression between FIGS. 5A-B, resilient fingers 134, 136 may be inserted over projections 40, 70 with sleeve 128 in its retracted position. Such position of sleeve 128 may, in one embodiment, correspond to the "remove" mode shown in FIG. 8A. Upon insertion of fingers 134, 136 over projections 40, 70, fingers 134, 136 may translate outwards to accommodate the shape of projections 40, 70. After full insertion of fingers 134, 136 over projections, angled surfaces 154 may seat within or accommodate the shape of projections 40, 70. Stated differently, since fingers 134, 136 may be biased to remain within the channels in shaft 122, after insertion of fingers 134, 136 over projections 40, 70, fingers 134, 136 may return to their normal un-translated state and conform to the shape of projections 40, 70. Such is shown in detail in FIG. 5B.

Figure 6A:
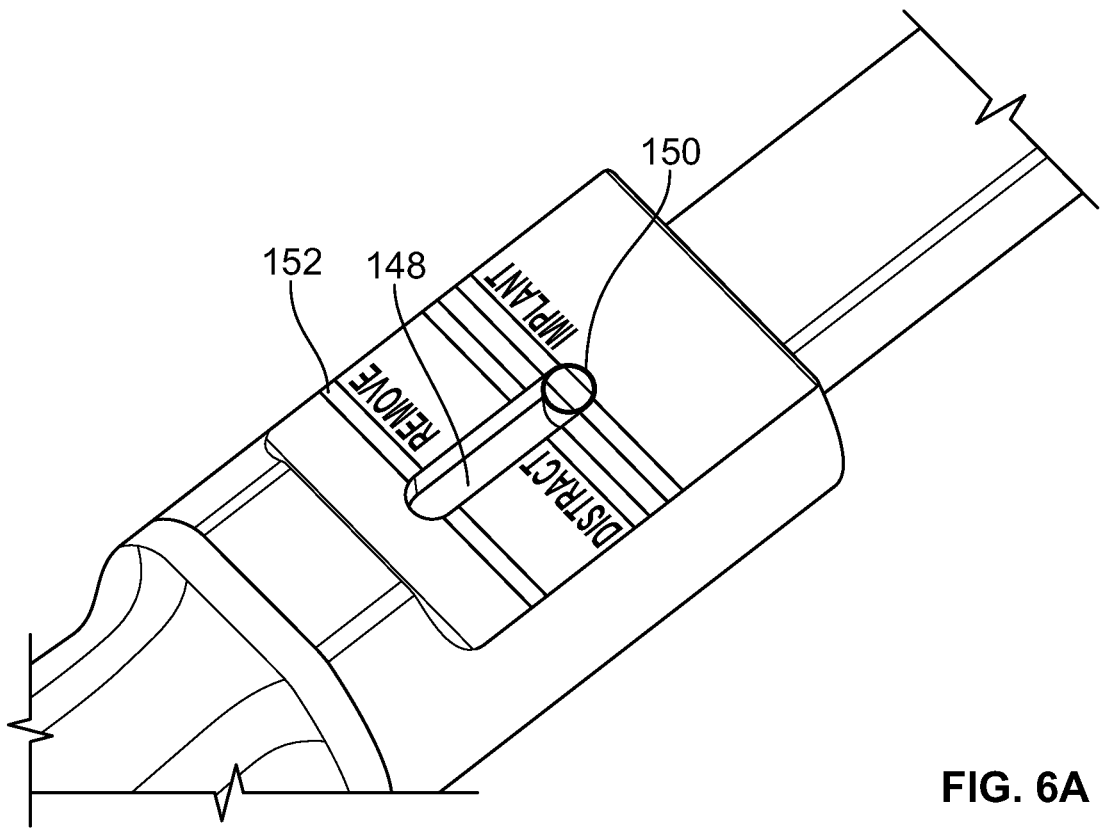
FIGS. 6A-B are perspective views of the instrument of FIGS. 4A-B, with the instrument configured for implantation of the implant.
Figure 6B:
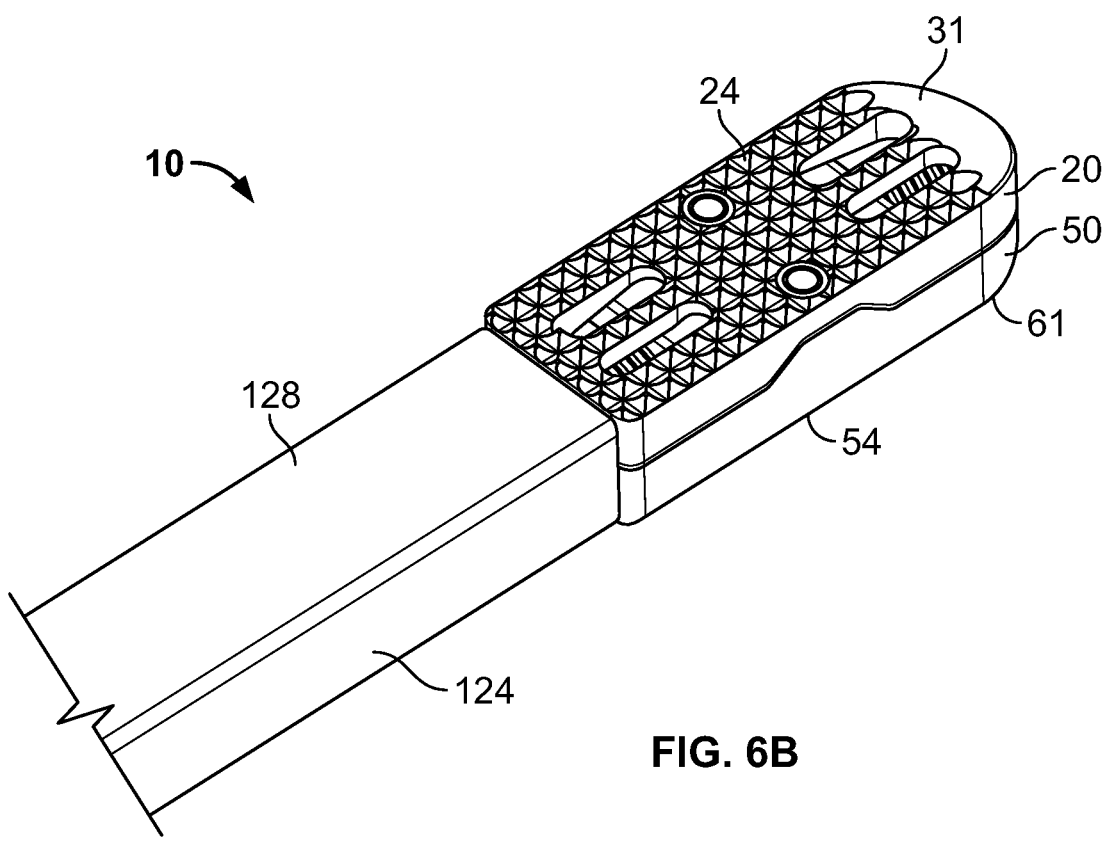

With socket 130 connected to engagement nut 90 and fingers 134, 136 situated about projections 40, 70, sleeve 128 of instrument 120 may then be translated longitudinally via knob 138 until such a point as sleeve 128 contacts implant 10, as shown in FIGS. 6A-B. This position of sleeve 128 may correspond to the "implant" mode of instrument 120, which may be indicated by the movement of indicator 150 within viewing window 148. In particular, movement of sleeve 128 may cause movement of indicator 150 within window 148, such that indicator 150 becomes aligned with a marking 152 corresponding to the "implant" mode of instrument 120, as shown in FIG. 6A. Further, as sleeve 128 moves longitudinally in the manner described above, fingers 134, 136 may be compressed against projections 40, 70, thereby securing instrument 120 to implant 10. Implant 10 may then be inserted into the intervertebral disc space via instrument 120, such that outer bone-contacting surfaces 24, 54 engage upper and lower vertebral bodies. The approach for implantation of implant 10, in some cases, may be a posterior or posterior-lateral approach, although other approaches are contemplated. In some embodiments, the vertebral bodies may also be prepared (e.g., through the use of cutting instruments) according to traditional spinal procedures prior to implantation of implant 10. It is also contemplated that, during insertion of implant 10, tapered ends 31, 61 of plates 20, 50 may provide easier insertion of implant 10 into the intervertebral space via insertion instrument 120. In addition, the lordotic angle between plates 20, 50 may, in one embodiment, accommodate lordosis of the adjacent vertebrae, if present.

Figure 7A:
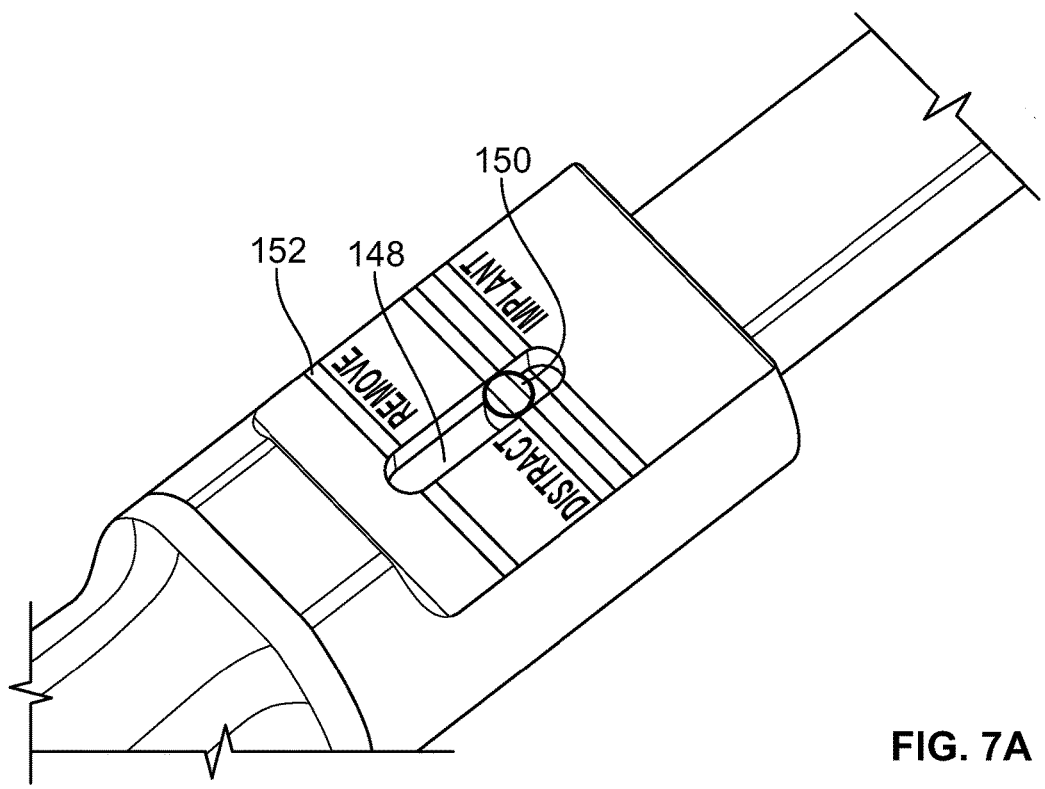
FIGS. 7A-B depict the instrument of FIGS. 4A-B, in which the instrument is configured for distraction of the implant.
Figure 7B:
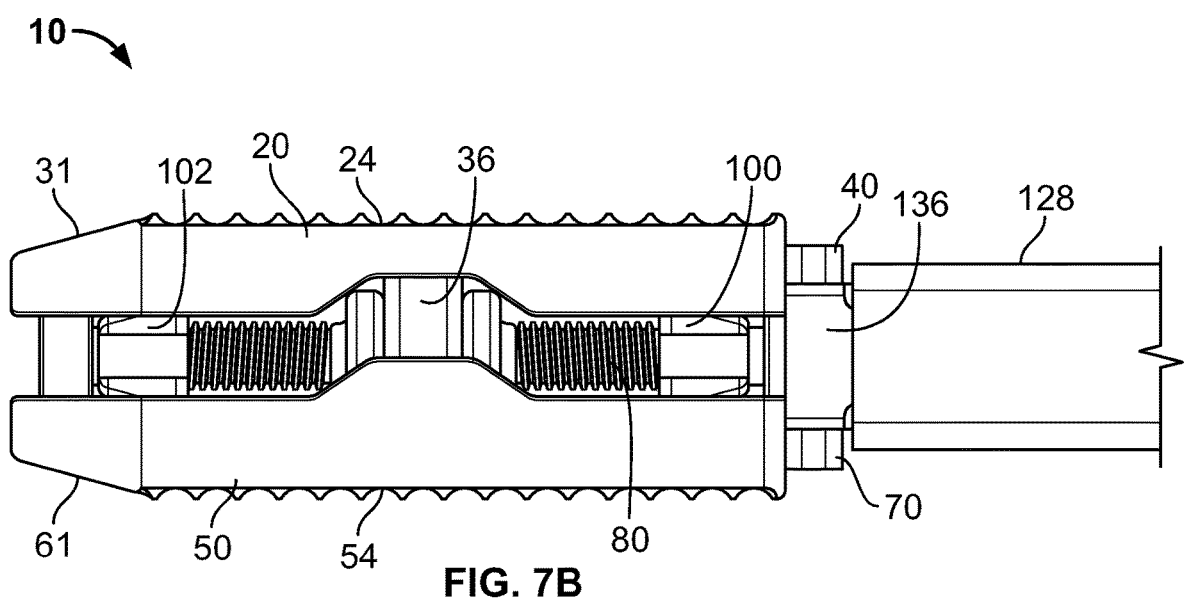

To distract implant 10 once inserted, instrument 120 may be placed in "distract" mode. Referring to FIGS. 7A-B, this involves rotating knob 138 in one direction to move the actuator and sleeve 128 toward proximal end 126 of instrument 120. As sleeve 128 moves toward proximal end 126, indicator 150 may also move within viewing window 148 so as to line up with the particular marking 152 corresponding to "distract" mode. Thus, a user may be informed when instrument 120 is placed in "distract" mode via rotation of knob 138. With sleeve retracted a sufficient distance towards proximal end 126, some pressure may be relieved from between fingers 134, 136 and projections 40, 70, thereby allowing plates 20, 50 to move apart from one another without fingers 134, 136 inhibiting such movement. Stated differently, sleeve 128 may be retracted towards proximal end 126, such that fingers 134, 136 may still retain projections 40, 70 and implant 10, but that pressure therebetween is somewhat relieved so as to allow distraction of implant 10. To achieve such distraction, the user may simply rotate handle 132 (FIG. 4A) causing socket 130 to rotate within engagement nut 90. This rotation of engagement nut 90, as described previously, may cause expansion members 100, 102 to interact with ramped surfaces 22, 52 of plates 20, 50 and force plates 20, 50 apart. Distraction of plates 20, 50 in this manner may also cause distraction of adjacent vertebral bodies. It is thusly possible for implant 10 to accommodate varying degrees of intervertebral spacing, as required during different surgeries or with different patients. Implant 10, in its expanded state as discussed above, is shown in detail in FIG. 7B.

Figure 8A:
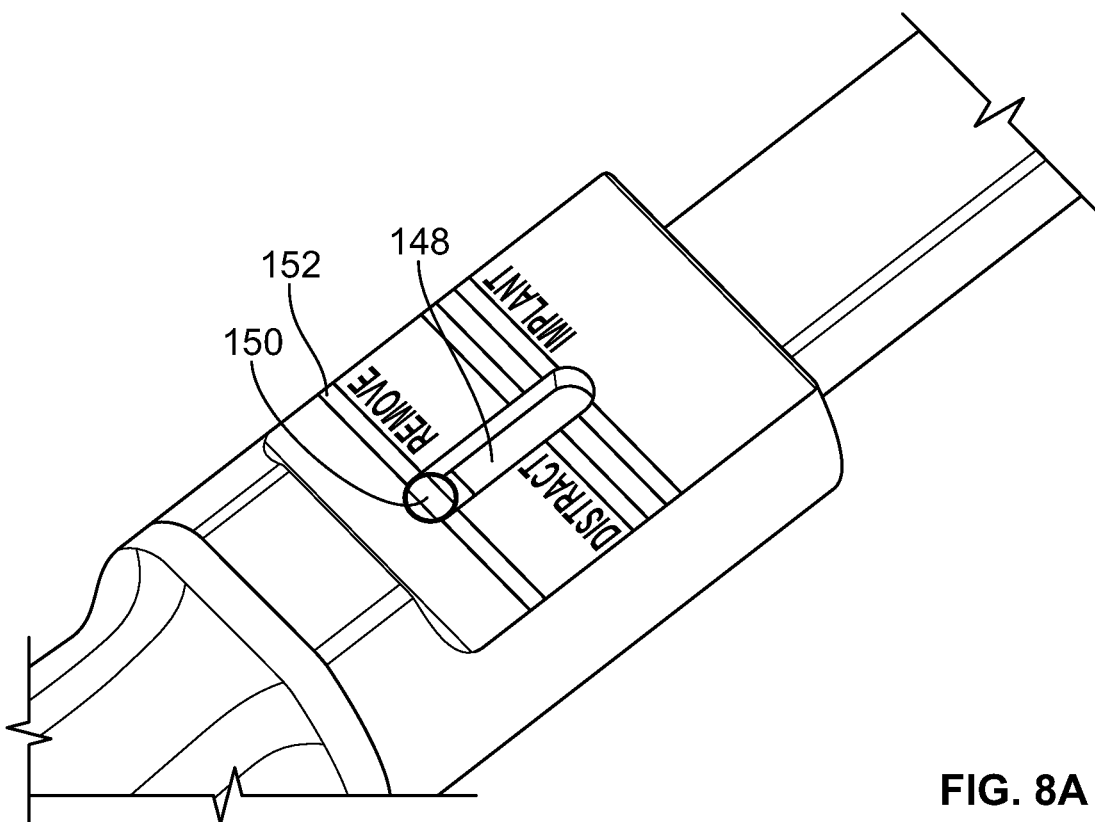
FIGS. 8A-B are perspective views of the instrument of FIGS. 4A-B, with the instrument configured to be removed from the implant.
Figure 8B:
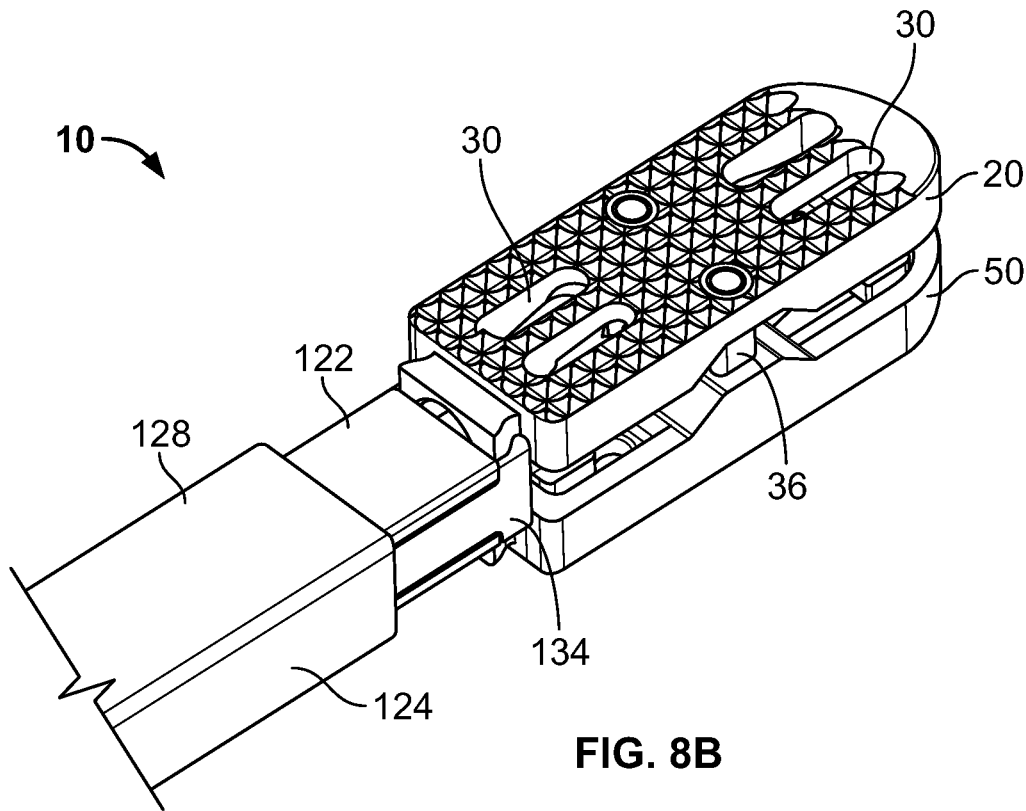

Referring now to FIGS. 8A-B, with implant 10 inserted into the intervertebral disc space, instrument 120 may be placed in "remove" mode, which again may be indicated by movement of indicator 150 within viewing window 148. In particular, knob 138 may be rotated in one direction causing movement of sleeve 128 towards proximal end 126 of instrument 120 and corresponding movement of indicator 150. Further, during movement of sleeve 128 towards proximal end 126, fingers 134, 136 may be fully released and allowed to resiliently deform outwards as instrument 120 is removed from about projections 40, 70. Instrument 120 may then be removed from the surgical site and implant 10 left to affect fusion of the adjacent vertebral bodies. To achieve improved fusion, it is also contemplated that bone-chips, synthetic graft material, or other biocompatible material may be inserted within the intervertebral disc space prior to or during the implantation of implant 10, and such material may adhere to the apertures in plates 20, 50 (e.g., apertures 30) provided for in-growth.

Figure 9:
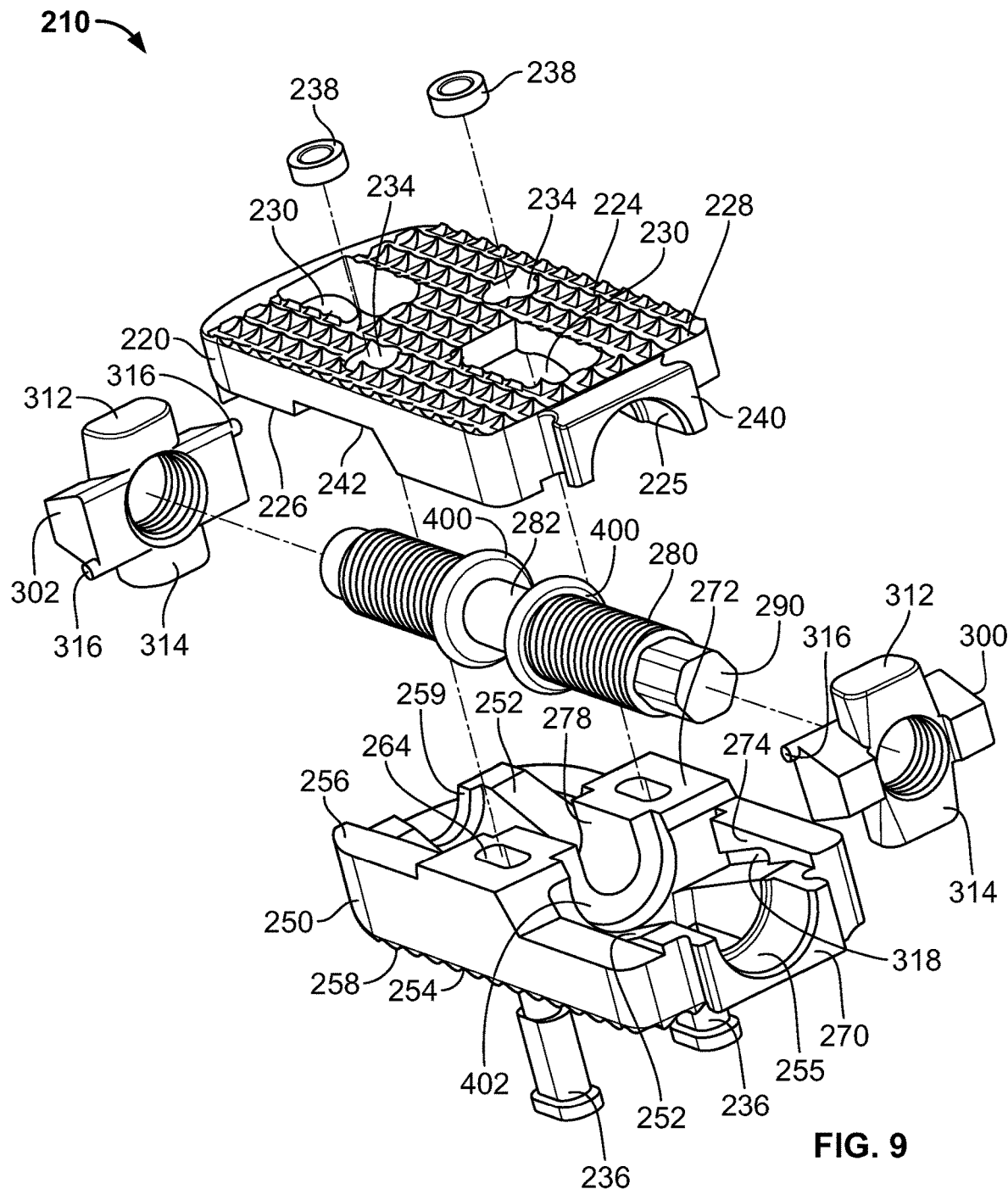
FIG. 9 is an exploded view of another embodiment of an expandable implant according to the present invention.
Figure 10A:
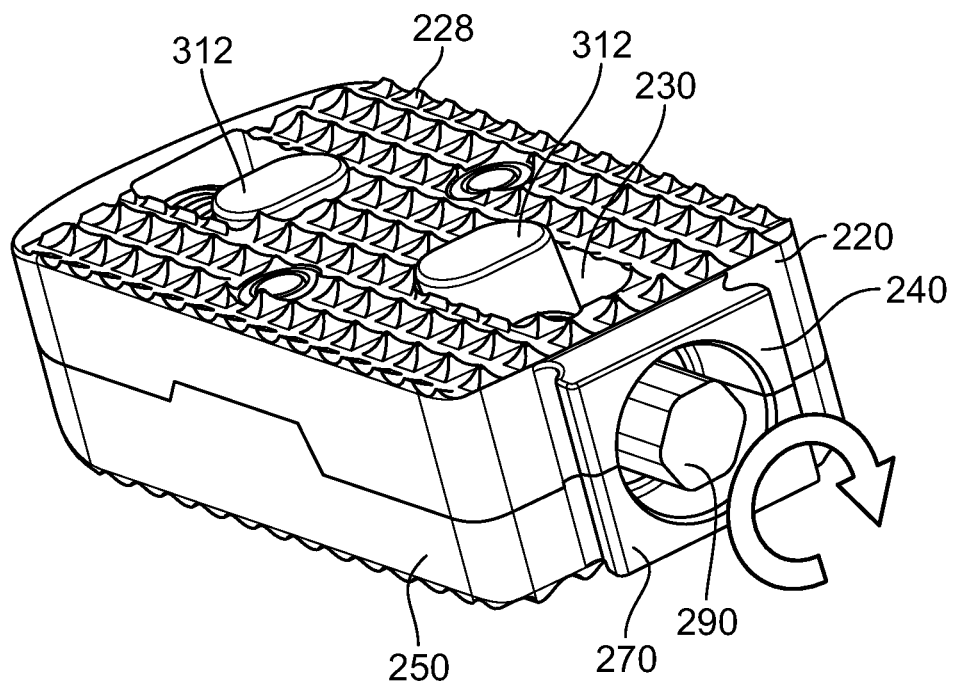
FIGS. 10A-B are perspective views of the implant of FIG. 9 in collapsed and expanded orientations, respectively.
Figure 10B:
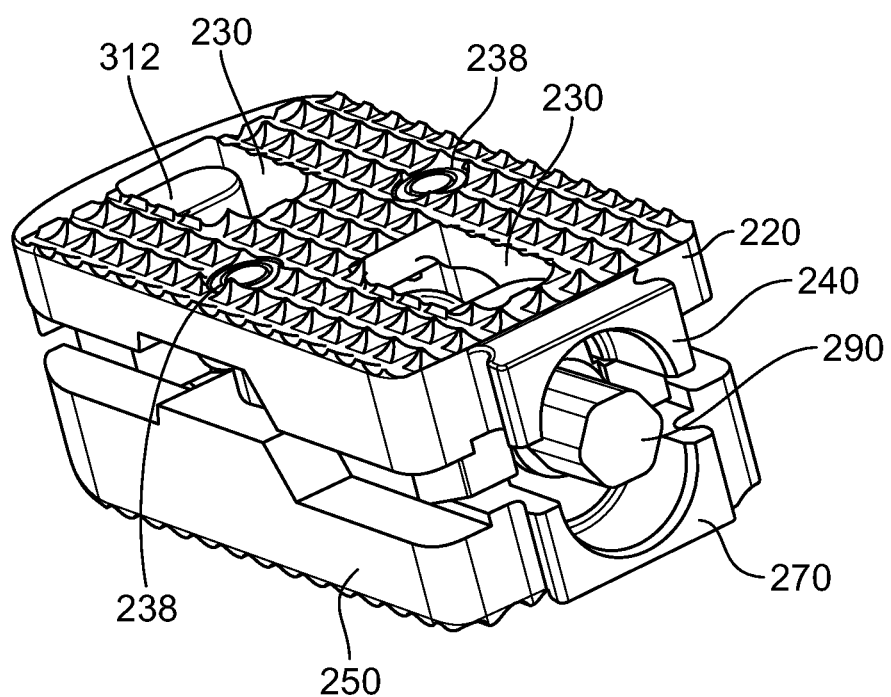

An alternate embodiment implant 210 is shown in FIG. 9. Due to the similarity between the structures of implants 10, 210, like numerals will refer to like elements and, predominantly, only the structural differences between implants 10, 210 will be highlighted. Thus, apart from the below-mentioned distinguishing features, it is contemplated that implants 10, 210 may have the same structure and may operate in the same manner (e.g., as set forth above) to accomplish the same purpose.

Referring to FIG. 9, implant 210 may include top and bottom plates 220, 250, such plates including, inter alia: (1) outer bone-contacting surfaces 224, 254 and opposed inner surfaces 226, 256; (2) projections 240, 270, which in one embodiment may be dovetail-shaped; (3) apertures 234, 264 for receiving posts 236 and nuts 238; (4) recessed and raised center portions 242, 272; and (5) angled surfaces 222, 252 for engaging with expansion members 300, 302. Other similar features to implant 10 are also present in implant 210; and, although not discussed in detail herein, such features are indicated by like reference numerals in the figures.

Several differentiating features of implant 210 will now be described, such features providing improvements in the operation of expandable implant 210. Referring to FIG. 9, implant 210 may include an axle 280 disposed between top and bottom plates 220, 250, with axle 280 including a center member 282 that is slightly different in shape than hourglass-shaped member 80 of implant 10. Even so, center member 282 of axle 280 may include opposed discs 400 for engaging with cutouts 402 formed in bottom plate 250, and a center portion having a reduced diameter for seating within cutout 278, as shown in detail in FIG. 12A. With center member 282 situated in bottom plate 250 as described, axle 280 may be longitudinally stabilized with respect to plate 250 (e.g., through the interaction of opposed discs 400 and cutouts 402), as is the case with axle 80 of implant 10.

Figure 11A:
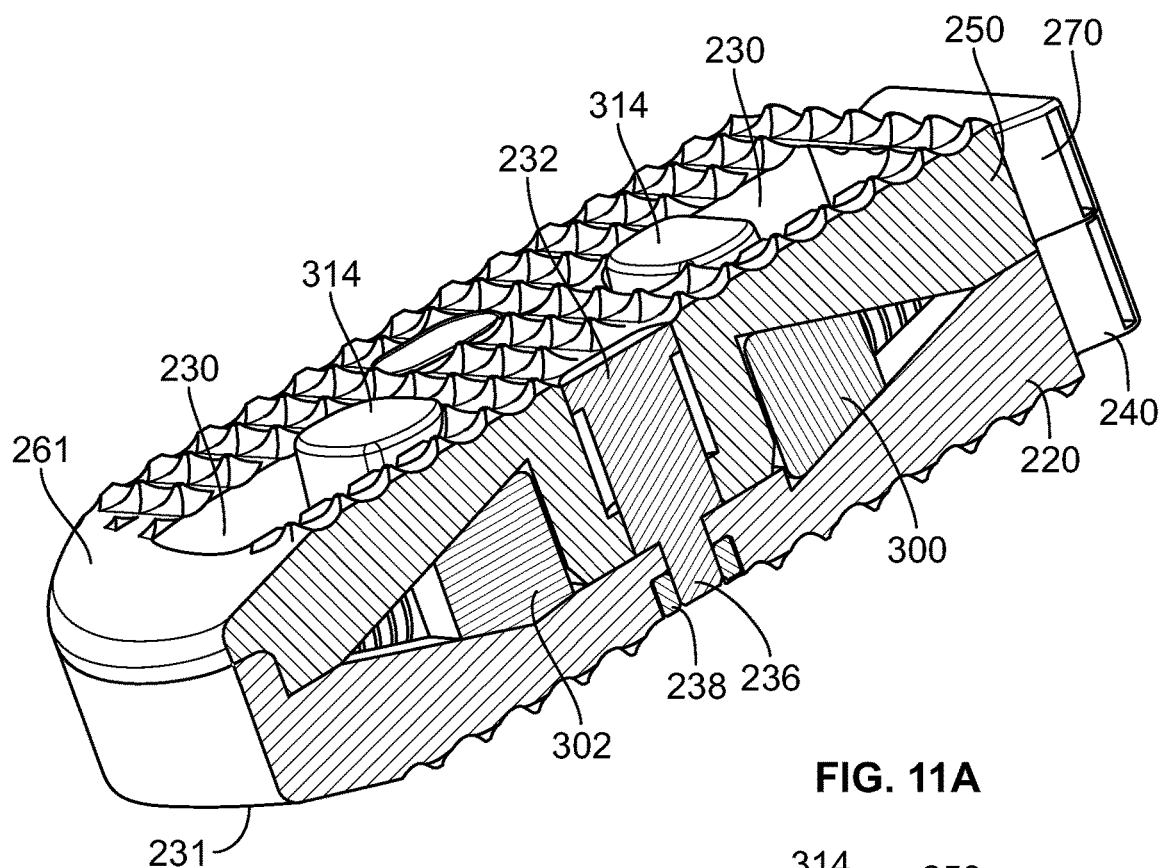
FIGS. 11A-B are cross-sectional views of the implant of FIGS. 10A-B.
Figure 11B:
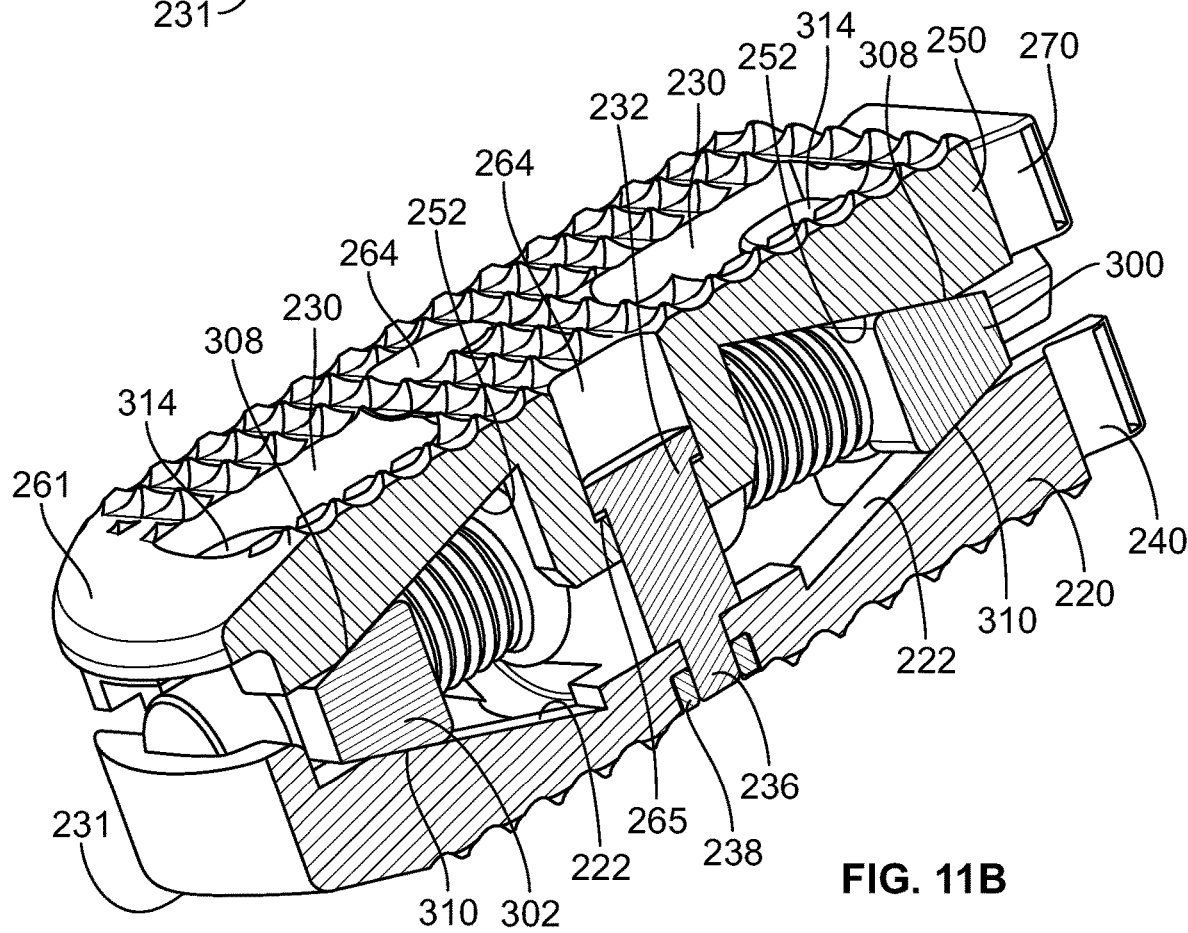

Implant 210 may also include expansion members 300, 302 having top and bottom surfaces 308, 310 that are angled in the manner described with reference to expansion members 100, 102, as shown in FIGS. 11A-B, but expansion members 300, 302 may also have vertically-extensive projections 312, 314 extending outward therefrom. Expansion members 300, 302 may also include a set (or one or more) of pins 316 extending from the sides of members 300, 302. Vertically-extensive projections 312, 314 of expansion members 300, 302 may be received in elongate apertures 230 formed in top and bottom plates 220, 250, such apertures 230 being configured to allow translation of vertically-extensive projections 312, 314 during expansion of implant 210. Pins 316 of expansion members 300, 302 may ride along slots 318 formed within side walls 244, 274 situated adjacent angled surfaces 222, 252 for guiding expansion members 300, 302 during expansion of implant 210, as shown in detail in FIGS. 9 and 12A-B.

In use, implant 210 may be implanted and/or expanded in much the same manner as implant 10. Particularly, it is contemplated that insertion instrument 120 may be modified only slightly to properly operate with and engage implant 210, and to distract such implant 210 after implantation. For example, while it is contemplated that engagement nut 290 of implant 210 may include Torx structure, it is shown in the figures as a hexagonal nut 290 (FIGS. 9, 11A-B). Thus, socket 130 of instrument 120 may be modified to accommodate this structure, and to engage with engagement nut 290 in the manner described in relation to implant 10. To be exact, such modified socket 130 may be inserted over engagement nut 290, and rotated via handle 132 so as to expand implant 210. It is also contemplated that instrument 120 may be placed into the various modes (e.g., "implant" mode, "distract" mode, and/or "remove" mode) upon engaging, distracting, and/or separating from implant 210, as discussed previously. Significantly, however, during expansion of implant 210 through the use of instrument 120, several structures of implant 210 may operate differently to provide a more stabilized and improved distraction procedure.

Figure 12A:
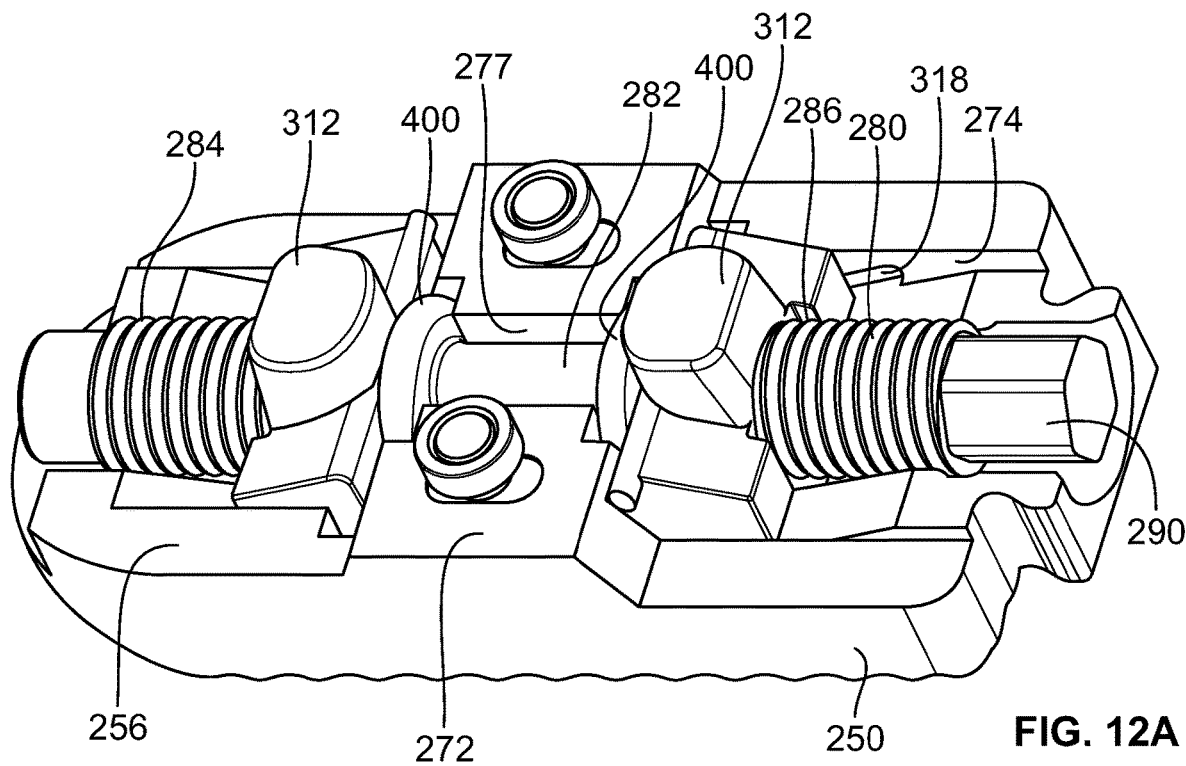
FIGS. 12A-B are exposed views of the bottom and top plates, respectively, of the implant of FIG. 9.
Figure 12B:
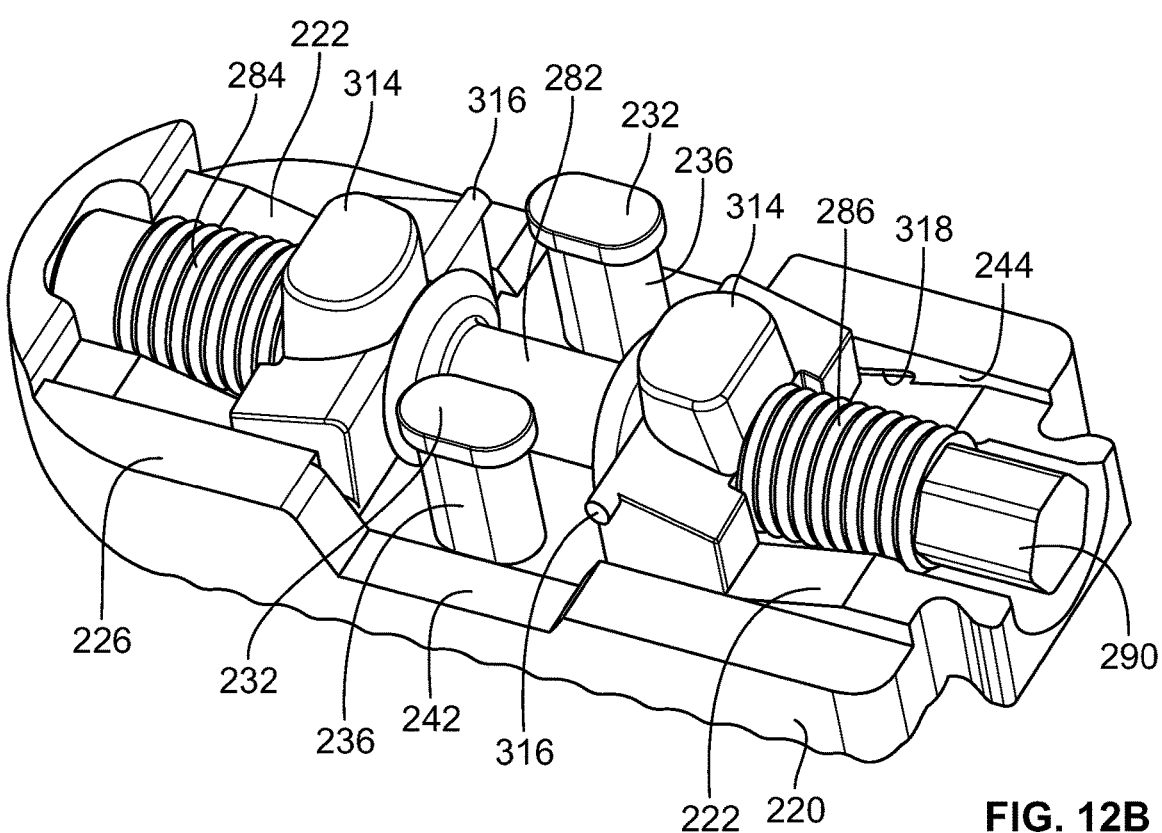

In one embodiment, referring now to FIGS. 9 and 12A-B, during expansion of implant 210 via the interaction between socket 130 and engagement nut 290, expansion members 300, 302 may engage with angled surfaces 222, 252; but, during separation of expansion members 300, 302 via the reverse threading of threaded sections 284, 286, pins 316 extending from expansion members 300, 302 may ride along slots 318 formed in respective side walls 244, 274 of top and bottom plates 220, 250. The engagement between pins 316 and slots 318 may act to stabilize the movement of expansion members 300, 302, and may also serve to limit the expansion of implant 210. Indeed, slots 318 may terminate at one section of side walls 244, 274, and pins 316 may abut this section upon full expansion of implant 210 to prohibit further movement of expansion members 300, 302 (e.g., away from one another). In one embodiment, pins 316 may be situated on diagonally opposite sides of each respective expansion member 300, 302, although it is contemplated that additional pins 316 may be used (e.g., on all four (4) corners of expansion members 300, 302). The engagement between pins 516 and slots 518 may also, at least partially, serve to keep plates 220, 250 in registration with one another during distraction.

An additional stabilization and/or expansion-limiting feature may be included with implant 210 in the form of elongate apertures 230. In particular, referring to FIGS. 10A-11B, during expansion of implant 210 via the use of instrument 120, vertically-extensive projections 312, 314 of expansion members 300, 302 may interact with elongate apertures 230 in top and bottom plates 220, 250 to stabilize such members 300, 302 and plates 220, 250. As shown in the progression between FIGS. 10A-10B and 11A-11B, vertically-extensive projections 312, 314 may be arranged within elongate apertures 230 of plates 220, 250; and, upon expansion of implant 210, vertically-extensive projections 312, 314 may translate within apertures 230, such that plates 220, 250 and expansion members 300, 302 are stabilized during distraction. Upon reaching an end of apertures 230, expansion members 300, 302 may also be limited from further outward movement. Apertures 230 may also, like apertures 30 of implant 10, operate to receive bone graft or other osteoinductive material to facilitate fusion of adjacent vertebral bodies upon implantation of implant 210. Although not discussed in detail herein, the remainder of steps pertaining to the implantation and/or expansion of implant 210, and its interaction with instrument 120, is again substantially identical to that discussed above with respect to implant 10.

Figure 13A:
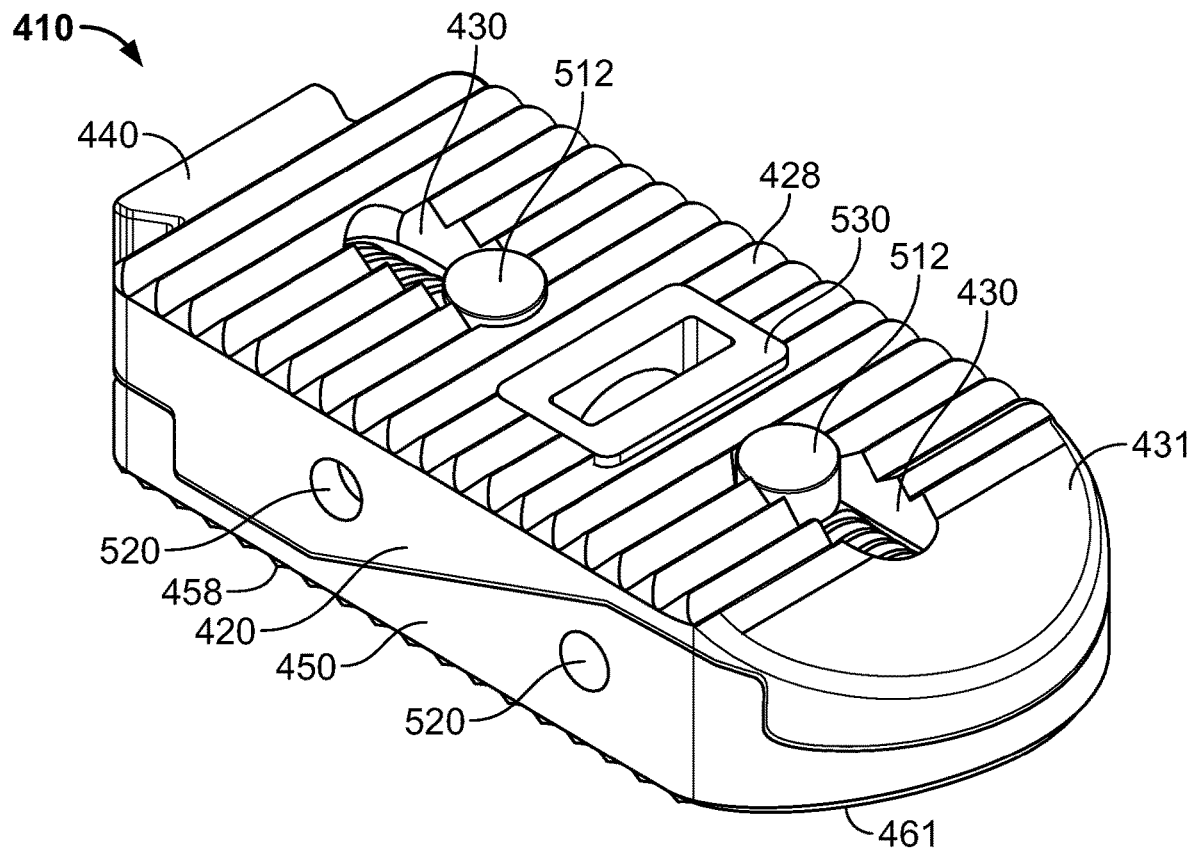
Figure 13B:
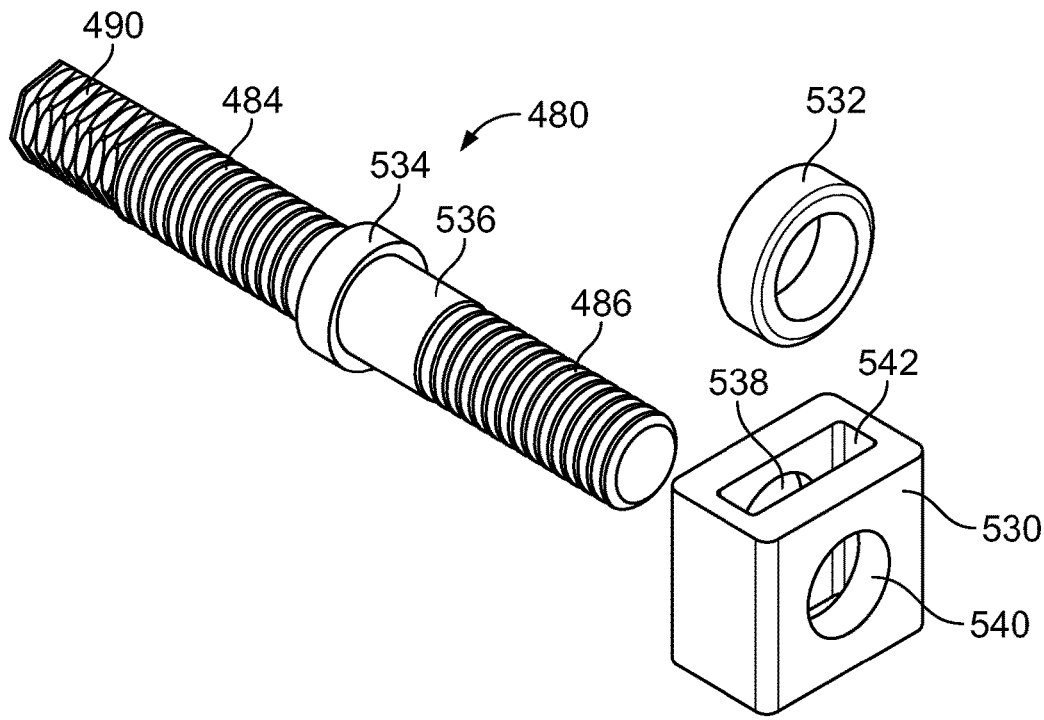
FIG. 13B is an exploded view of the distraction mechanism used with that implant.
Figure 14:
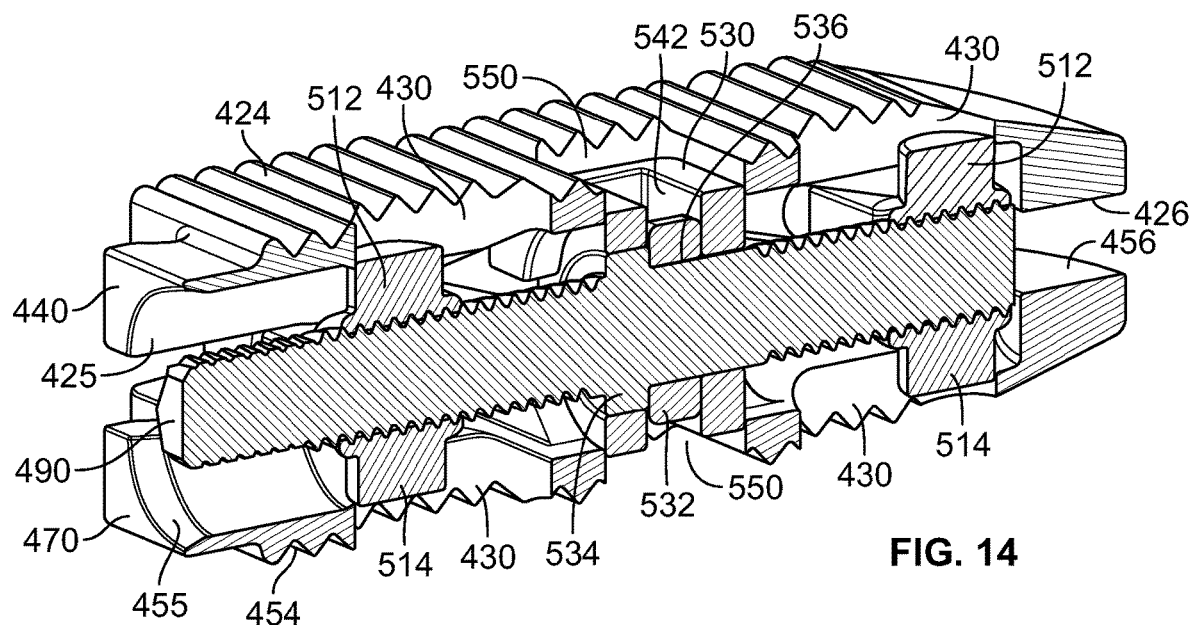
FIG. 14 is a cross-sectional view of the implant of FIG. 13A.
Figure 15:
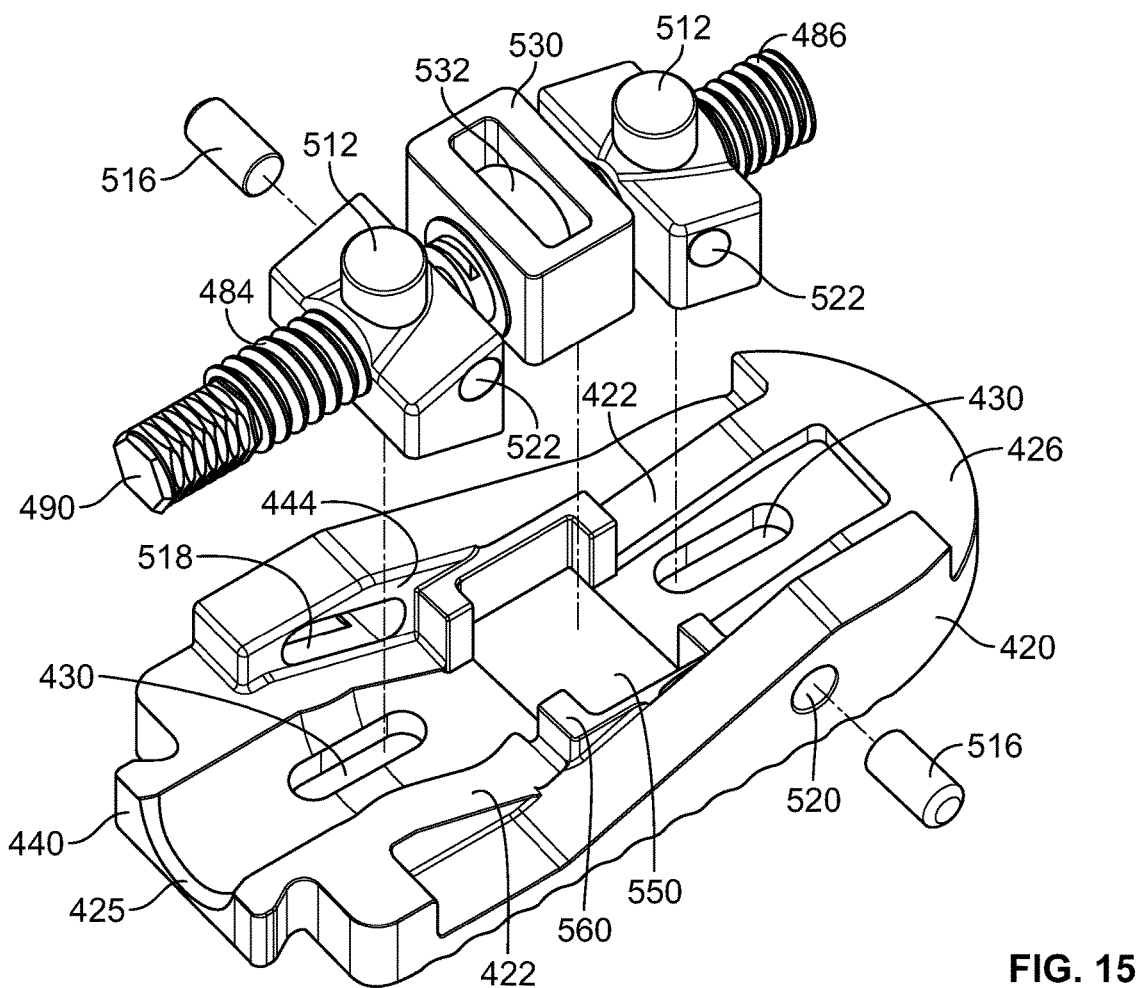
FIG. 15 is an exposed view of one of the plates of the implant of FIG. 13A, the other plate being a mirror image thereof.

Another embodiment of an expandable implant, implant 410, is shown in FIGS. 13A-15. Here, like numerals will refer to like elements, with the structural differences between implants 10, 210, 410 being discussed. Thus, as with above, apart from the distinguishing features detailed in subsequent sections, it is contemplated that implants 10, 210, 410 may have the same structure and operate in the same manner to accomplish the same purpose. Here, it is worthwhile to note that, while FIG. 15 only depicts top plate 420, bottom plate 450 is a mirror image thereof, and thus, FIG. 15 is an accurate representation of both plates 420, 450 (e.g., with like reference numerals referring to like elements).

Referring to FIGS. 13A and 15, implant 410 may include top and bottom plates 420, 450 with angled inner surfaces 422, 452 for engaging with expansion members 500, 502, much like implants 10, 210. Further, expansion members 500, 502 of implant 410 may also include vertically-extensive projections 512, 514 for engaging with elongate apertures 430 in plates 420, 450, such that upon expansion of implant 410, vertically-extensive projections 512, 514 may translate within apertures 430. Other similar features to implants 10, 210 are also included with implant 410, such as: (1) outer bone-contacting surfaces 424, 454 with teeth or serrations 428, 458; (2) tapered ends 431, 461 of plates 420, 450; (3) dovetail-shaped projections 440, 470; (4) slots 518 in side walls 444, 474 of plates 420, 450; and (5) expansion members 500, 502 including pins 516 for engaging with slots 518. Yet, other features, such as the distraction mechanism of implant 410, may operate differently than found with implants 10, 210.

Referring to FIG. 13B, the distraction mechanism of implant 410 may include a rod or axle 480, a capture mechanism 530, and a containment ring 532. Axle 480, like axles 80, 280, may be threaded in one embodiment, and may include separate sections 484, 486 with left-handed and right-handed threads. An engagement nut 490 structure may also be disposed on one end of axle 480, and a center of axle may include a radially-extending flange 534 and a press-fit region 536.

Capture mechanism 530 may include a set of apertures 538, 540 for receiving a portion of axle 480, and a slot 542 for receiving containment ring 532. Slot 542 may be dimensioned to allow free movement of containment ring 532 and axle 480 once situated therein. In one embodiment, aperture 538 of capture mechanism 530 may have a diameter that is larger than aperture 540 so as to allow flange 534 to be received in aperture 538. Further, each aperture 538, 540 may be smaller in diameter than an outer diameter of containment ring 532. In a particular embodiment, containment ring 532 includes an inner diameter such that, upon insertion of press-fit region 536 into containment ring 532, a dimensional interference is established therebetween.

Apart from the differences between distraction mechanisms amongst implants 10, 210, 410, implant 410 may also include plates 420, 450 with apertures 550 for receiving a portion of capture mechanism 530, as shown in FIG. 14. Inner surfaces 426, 456 of plates 420, 450 may also include structure (e.g. a housing 560) for stabilizing capture mechanism 530 (and thus axle 480) in a longitudinal direction, as shown in FIG. 15. In one embodiment, plates 420, 450 also include openings 520 through which pins 516 may be inserted. Similarly, expansion members 500, 502 may include openings 522 for receiving pins 516.

In use, the distraction mechanism of implant 410 may be situated between plates 420, 450 such that axle 480 is inserted into capture mechanism 530 and through containment ring 532, as shown in FIG. 14. In particular, containment ring 532 may be disposed within slot 542 in capture mechanism 530, and axle 480 may be inserted through apertures 538, 540. To be exact, axle 480 may be inserted through containment ring 532 until such a point as press-fit region 536 is situated within containment ring 532 and flange 534 is housed within aperture 538 and abuts containment ring 532. In this orientation, press-fit region 536 may interact with containment ring 532 to establish a dimensional interference between such structures, such that axle 480 may be securely retained within capture mechanism 530. To be exact, the interaction between flange 534 and containment ring 532 may prevent movement of axle 480 in one direction, and the cooperation between press-fit region 536, containment ring 532, and slot 542 may prevent movement of axle 480 in another opposing direction. With axle situated in capture mechanism 530 in the manner described above, capture mechanism 530 may then be inserted into apertures 550 in plates 420, 450.

Capture mechanism 530, axle 480, and expansion members 500, 502 may be situated between plates 420, 450, with the inner surfaces 426, 456 of plates 420, 450 facing one another, as discussed above, and pins 516 may be inserted through openings 520 in plates 420, 450 and into openings 522 in expansion members 500, 502. Indeed, pins 516 may be press-fit into openings 522 in expansion members 500, 502, such that pins 516 are firmly retained in expansion members 500, 502. Pins 516 are also designed to ride within slots 518 to limit movement of expansion members 500, 502, and such pins 516 may also serve to keep plates 420, 450 firmly connected together. In other words, as at least one pin 516 on each expansion member 500, 502 engages with a slot 518 in top plate 420, and at least one pin 516 with a slot 518 in bottom plate 450, such plates 420, 450 may be securely retained together via the interaction between pins 516 and slots 518. A terminal portion of slots 518 may also serve to prevent over-expansion of implant 410, as discussed above with respect to implant 210.

Implant 410 may also interact with instrument 120 in the same manner as implants 10, 210 (e.g., for purposes of implantation and/or distraction). For instance, rotation of handle 132 with respect to engagement nut 490 in one direction may cause expansion members 500, 502 to move outwardly, and pins 516 to engage with slots 518. Such movement of expansion members 500, 502 may also cause outward movement or distraction of plates 420, 450, as with implants 10, 210; and additional rotation of handle 132 may cause pins 516 of expansion members 500, 502 to engage with a terminal portion of slots 518 to prevent further outward movement of expansion members 500, 502.

What is more, during the aforementioned movement of expansion members 500, 502, vertically-extensive projections 512, 514 may translate within apertures 430 in plates 420, 450, and apertures 550 in plates 420, 450 may interact with capture mechanism 530. Stated differently, as expansion members 500, 502 engage with angled surfaces 422, 522 to distract implant 410 (e.g., via use of instrument 120), apertures 550 in plates 420, 450 may slide along portions of capture mechanism 530, vertically-extensive projections 512, 514 may translate within apertures 430, and pins 516 may ride within slots 518. Such movement of expansion members 500, 502 may therefore serve to stabilize implant 410 during distraction. For instance, the interaction between vertically-extensive projections 512, 514 and apertures 430, and apertures 550 and capture mechanism 530, may provide torsional and/or compressive stability to implant 410 during distraction, and pins 516 may act as distraction-limiting features. Thus, as with implants 10, 210, implant 410 may provide an expandable implant with improved features for maintaining stability and/or controlling distraction during replacement of an intervertebral disc.

In the devices shown in the figures, particular structures are shown as being adapted for use in the implantation, distraction, and/or removal of an expandable implant according to the present invention(s). The invention(s) also contemplates the use of any alternative structures for such purposes, including structures having different lengths, shapes, and/or configurations. For example, as alluded to above, although certain structures are used for socket 130 and engagement nut 90, 290, 490 (e.g., Torx or hexagonal), it is contemplated that a variety of different socket/nut combinations may be used, such as square, triangular, etc.

In addition, while angled surfaces 22, 52, 222, 252, 422, 452 are shown in the figures as being predominantly flat, it is also contemplated that surfaces 22, 52, 222, 252, 422, 452 may be curved in one embodiment so as to facilitate expansion of implants 10, 210, 410. Top and bottom surfaces 108, 110, 308, 310, 508, 510 of expansion members 100, 102, 300, 302, 500, 502 may likewise be shaped to accommodate the curvature of angled surfaces 22, 52, 222, 252, 422, 452, as previously discussed with respect to implants 10, 210, 410.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. An expandable intervertebral implant comprising:
   top and bottom plates each having inner and outer surfaces and a ramp surface, at least one of the top and bottom plates having an opening extending through the inner and outer surfaces;
   a rotatable actuator positioned between the inner surfaces of the top and bottom plates; and
   first and second expansion members engageable with the actuator and positioned between the inner surfaces of the top and bottom plates, at least one of the first and second expansion members having an engagement surface configured to engage a respective one of the ramp surfaces and a vertical projection extending beyond the engagement surface,
   wherein rotation of the actuator in opposing directions causes the first and second expansion members to move toward and away from each other along a longitudinal axis of the actuator such that the at least one vertical projection of the first and second expansion members translates within the opening relative to the actuator, the movement of the first and second expansion members causing the top and bottom plates to move toward and away from each other within a vertical plane extending along the longitudinal axis of the actuator.

2. The implant of claim 1, wherein a perimeter of the at least one opening is fully enclosed within the top plate or the bottom plate.

3. The implant of claim 1, wherein the actuator includes an engagement nut at a proximal end thereof.

4. The implant of claim 3, wherein the engagement nut is adapted to be engaged by an insertion instrument.

5. The implant of claim 1, wherein the at least one opening of the top and bottom plates is disposed adjacent the respective ramp surface of the top and bottom plate.

6. The implant of claim 1, wherein the actuator includes first and second threaded portions, the first and second threaded portions having oppositely facing threads configured to engage threads of the first and second expansion members, such that when the actuator is rotated, the first and second expansion members move along the longitudinal axis of the actuator in opposite directions.

7. The implant of claim 1, wherein the first and second expansion members each have a lateral projection receivable within a corresponding lateral slot on each of the top and bottom plates.

8. The implant of claim 7, wherein the lateral slots are disposed adjacent respective ramp surfaces of the top and bottom plates.

9. The implant of claim 1, wherein the first and second expansion members translate along a longitudinal axis of the implant.

10. The implant of claim 1, wherein the implant is moveable between a first condition and an operative condition, wherein, in the first condition, the first and second expansion members are positioned relatively close to each other along the longitudinal axis of the actuator and the top and bottom plates are positioned relatively close together along the vertical axis, and wherein, in the operative condition, the first and second expansion members are positioned relatively farther away from each other along the longitudinal axis and the top and bottom plates are positioned relatively farther away from each other along the vertical axis than in the first condition.

11. A method of implanting an expandable intervertebral implant comprising:
   implanting an expandable intervertebral implant having top and bottom plates within a spinal column;
   rotating an actuator positioned between inner surfaces of the top and bottom plates so that a first expansion member engages the actuator and moves in a first direction and a second expansion member engages the actuator and moves in a second direction opposite the first direction, such that engagement surfaces of the expansion member engages ramp surfaces of the top and bottom plates thereby causing the top and bottom plates to move away from each other; and translating a vertical projection of at least one of the first and second expansion members within an opening extending through inner and outer surfaces of at least one of the top plate and the bottom plate while the first expansion member moves in the first direction and the second expansion member moves in the second direction, the vertical projection extending beyond the engagement surface of the expansion member.

12. The method of claim 11, wherein during the rotating step, the engagement surfaces the first and second expansion members are angled surfaces that engage the ramp surfaces of the inner surfaces of the top and bottom plates.

13. The method of claim 11, wherein the first and second expansion members translate alongside a longitudinal axis of the actuator.

14. The method of claim 13, wherein the longitudinal axis of the actuator extends alongside a longitudinal axis of the implant.

15. The method of claim 11, wherein the first and second expansion members each have a pair of vertical projections extending beyond engagement surfaces.

16. The method of claim 11, further comprising translating lateral projections within slots of the implant.

17. The method of claim 11, further comprising engaging a tool to the actuator, wherein the step of rotating the actuator comprises rotating the actuator with the tool.

18. The method of claim 11, wherein the step of implanting includes engaging the top and bottom plates of the implant with first and second adjacent vertebral bodies of the spinal column, and further comprising the step of moving the first and second adjacent vertebral bodies away from each other while the first expansion member moves in the first direction and the second expansion member moves in the second direction.

19. The method of claim 11, wherein the at least one opening has a perimeter fully enclosed within the top plate or the bottom plate.

20. The method of claim 11, wherein during the rotating step, the top and bottom plates move away from each other within a vertical plane extending along a longitudinal axis of the actuator.

* * * * *